US012569606B2

(12) United States Patent
Peritt et al.

(10) Patent No.: US 12,569,606 B2
(45) Date of Patent: Mar. 10, 2026

(54) CLOSED LOOP, BEDSIDE CELL PURIFICATION SYSTEMS AND METHODS

(71) Applicant: LUPAGEN, INC., Irving, TX (US)

(72) Inventors: David Peritt, Irving, TX (US); Nripendra Das, Irving, TX (US)

(73) Assignee: Lupagen, Inc., Irving, TX (US)

( * ) Notice: Subject to any disclaimer, the term of this patent is extended or adjusted under 35 U.S.C. 154(b) by 305 days.

(21) Appl. No.: 18/247,608

(22) PCT Filed: Oct. 1, 2021

(86) PCT No.: PCT/US2021/053242
§ 371 (c)(1),
(2) Date: Mar. 31, 2023

(87) PCT Pub. No.: WO2022/072885
PCT Pub. Date: Apr. 7, 2022

(65) Prior Publication Data
US 2024/0016991 A1     Jan. 18, 2024

Related U.S. Application Data

(60) Provisional application No. 63/087,096, filed on Oct. 2, 2020.

(51) Int. Cl.
*A61M 1/36* (2006.01)
*A61M 1/34* (2006.01)

(52) U.S. Cl.
CPC .......... *A61M 1/362* (2014.02); *A61M 1/3496* (2013.01); *A61M 1/3618* (2014.02); *A61M 2205/3306* (2013.01)

(58) Field of Classification Search
CPC .... A61M 1/36; A61M 1/3681; A61M 1/3601; A61M 1/0209; A61M 1/0213; A61M 1/3683; A61M 2205/128; A61M 1/3686; A61M 1/3692
See application file for complete search history.

(56) References Cited

U.S. PATENT DOCUMENTS

| | | | |
|---|---|---|---|
| 2004/0014693 A1 | 1/2004 | Muggetti et al. | |
| 2010/0210989 A1 | 8/2010 | Machperson et al. | |
| 2013/0197419 A1* | 8/2013 | Min .................... | A61M 1/3681 |
| | | | 422/44 |
| 2015/0219636 A1 | 8/2015 | Rychak et al. | |
| 2019/0060548 A1 | 2/2019 | Peritt et al. | |
| 2021/0146030 A1* | 5/2021 | Josephs ............... | A61M 1/3679 |
| 2022/0143291 A1* | 5/2022 | Poirier ..................... | A61P 7/00 |

FOREIGN PATENT DOCUMENTS

| | | |
|---|---|---|
| CA | 3100050 | 11/2019 |

* cited by examiner

*Primary Examiner* — Rebecca E Eisenberg
*Assistant Examiner* — Alessandro R Del Priore
(74) *Attorney, Agent, or Firm* — Rimon PC

(57) ABSTRACT

Provided herein are bedside, parenterally patient connected, closed-loop and complete systems and methods for cell purification.

11 Claims, 4 Drawing Sheets

FIG. 1

Electromagnetic
element (12)

Separation chamber
disposable unit (13)

Electromagnetic
element (12)

CLOSED LOOP, BEDSIDE CELL PURIFICATION SYSTEMS AND METHODS

This application is a National Stage Application of International Application No. PCT/US2021/053242 filed on Oct. 1, 2021, which claims priority to and the benefit of U.S. Provisional Application No. 63/087,096, filed on Oct. 2, 2020, both of which are incorporated herein in their entirety by reference for all purposes as if fully set forth herein.

BACKGROUND OF THE INVENTION

Autologous cell and gene therapy (ACGT) enables the use of patients own cells manipulated for therapeutic benefit. Manufacturing of immune ACGT is currently conducted in centralized manufacturing or hospital based GMP facilities from blood or leukopheresis product. The manufacturing processes have complex supply chains, are cumbersome, and expensive due to the handling and regulatory agency mandated testing requirements. Bringing the process to the bedside in a patient connected manner has significant cost and safety benefits but comes with significant limitations including in the ability to enrich specific cell populations. Numerous methods for cell isolation and enrichment are currently employed in research and cell therapy manufacturing, but they have a variety of limitations and drawbacks and safety considerations that would require being addressed if contemplated in a patient connected system. This disclosure addresses the considerations necessary to bring the cell enrichment portion of the closed loop patient connected system bedside.

The present methods and systems address these and other needs in the art.

SUMMARY

Provided herein are bedside systems and methods for performing customized cell purification in a patient-connected, closed-loop continuous-flow manner. These systems and methods may be part of a larger system for cell therapy in the same closed-loop, bedside manner in which cells are further manipulated to enhance the therapeutic benefit.

In this regard, patient-connected, closed-loop system for the purification of a target cell from a patient sample is provided, the exemplary system including an inlet conduit adapted for parenteral communication with the patient and adapted for receiving blood from the patient; an apheresis or leukopheresis module in fluid connection with the inlet conduit; a targeting reagent comprising a substrate bound to a targeting moiety, wherein the targeting moiety is adapted to specifically bind or associate with the target cell; a cell purification module in fluid communication with the apheresis or leukopheresis module, the cell separation module comprising a mixing chamber configured to include at least one mixing chamber inlet fluidly coupled with the mixing chamber, wherein the at least one mixing chamber inlet is configured to store, guide or transport a liquid sample, the targeting reagent, or a combination of the liquid sample and the targeting reagent, to the mixing chamber; the mixing chamber further configured to include at least one mixing chamber outlet; a mixing mechanism coupled with the mixing chamber and adapted to mix (e.g., rock, shake, or agitate) a content of the mixing chamber; a collection chamber fluidly coupled with the at least one mixing chamber outlet, the collection chamber configured to include a collection chamber outlet, wherein the collection chamber is adapted to hold or transport a solution containing the target cell; a detector configured to conduct an evaluation comprising a detection operation of a solution that has passed through the at least one mixing chamber outlet or the collection chamber outlet; at least one cell purification module outlet adapted to direct a solution from the at least one mixing chamber outlet or from the collection chamber outlet to the patient for parenteral administration of the solution or to a transfection module for modification of the target cell; a system outlet conduit in parenteral communication with the patient; and a processor configured to control an operation of the inlet conduit and/or the cell purification module; wherein the inlet conduit, each aspect of the cell purification module, the cell customization module, and the system outlet conduit are connected in a fluid-sealed closed-loop adapted for parenteral connection with the patient at both ends of the fluid sealed closed-loop, and the system is configured to permit obtaining the sample, cell purification to produce purified cells, and delivery of the purified cells to the patient within the fluid-sealed closed-loop.

In other frequent embodiments, a patient-connected, closed-loop system for the purification of a target cell from a patient sample is provided, this system includes, for example, an inlet conduit adapted for parenteral communication with the patient and adapted for receiving blood from the patient; an apheresis or leukopheresis module in fluid connection with the inlet conduit; a targeting reagent comprising a substrate bound to a targeting moiety, wherein the targeting moiety is adapted to specifically bind or associate with the target cell; a cell purification module in fluid communication with the apheresis or leukopheresis module, the cell separation module comprising a separation chamber configured to include at least one separation chamber inlet fluidly coupled with the separation chamber, wherein the at least one separation chamber inlet is configured to store, guide or transport a liquid sample, the targeting reagent, or a combination of the liquid sample and the targeting reagent, to the separation chamber; the separation chamber further configured to include at least one separation chamber outlet; a detector configured to conduct an evaluation comprising a detection operation of a solution that has passed through the separation chamber outlet; at least one cell purification module outlet adapted to direct a solution from the at least one separation chamber outlet to the patient for parenteral administration of the solution or to a transfection module for modification of the target cell; a system outlet conduit in parenteral communication with the patient; and a processor configured to control an operation of the inlet conduit and/or the cell purification module; wherein the inlet conduit, each aspect of the cell purification module, the cell customization module, and the system outlet conduit are connected in a fluid-sealed closed-loop adapted for parenteral connection with the patient at both ends of the fluid sealed closed-loop, and the system is configured to permit obtaining the sample, cell purification to produce purified cells, and delivery of the purified cells to the patient within the fluid-sealed closed-loop.

Often in the embodiments contemplated herein, the system further comprises an electromagnetic element positioned and configured adjacent to the separation chamber and adapted to apply a magnetic field to a content of the separation chamber. Often, a pump is provided and configured in operable communication with the at least one mixing chamber outlet or the at least one separation chamber outlet. Frequently, the at least one mixing chamber outlet comprises a first and a second mixing chamber outlet, wherein the first mixing chamber outlet is fluidly coupled with the collection chamber, and the second mixing chamber outlet is fluidly coupled directly with the system outlet or the at least one mixing chamber inlet.

Often in the embodiments contemplated herein, the targeting moiety is an antibody having a specificity for a cell surface marker. Generally, this cell surface marker will be a marker that is selectively expressed or otherwise present in a target cell population. The specificity is as further described herein, with the antibody being capable of selectively or specifically binding the cell surface marker. In certain embodiments, the binding is binding that is tolerant of stringent conditions as those are known in the art. In certain embodiments, the binding is highly specific such that the cell surface marker is bound by the antibody to the exclusion of cells that do not have the cell surface marker.

In certain embodiments, the detector comprises an opacity sensor, a temperature sensor, a pH sensor, a pressure sensor, a magnetic field sensor, a chemical sensor, a cell-selective sensor, a fluorescence sensor, a luminescence sensor, a mass sensor, or a combination of two or more of the foregoing. In certain embodiments, the sensor is operably connected with a processor adapted to conduct an inquiry of the information obtained from the sensor using one or more machine learning algorithms or protocols to discern specific information about the data collected by the sensor.

Frequently, the evaluation comprises detecting a concentration or number of target cells, evaluating the sample for the presence or absence of the substrate, evaluating the sample for the percentage or amount of enrichment of the target cell in the sample.

In certain embodiments, the system further comprises a cell customization module. Often the system further comprises an apheresis module or a leukopheresis module positioned in-line between the inlet conduit and the cell purification module and in fluid communication with the inlet conduit and the cell purification module.

Often the substrate comprises a microbubble, a microparticle, a bead, and/or a nanoparticle. Often, the microbubble, a microparticle, a bead, and/or a nanoparticle is not a DYNAL bead.

According to frequent embodiments, the substrate is or comprises a functionalized microbubble comprising one or more reactive groups, linkers, ligands, or targeting moieties adapted for specific binding to a target cell. Often, the functionalized microbubble comprises a ligand present on the microbubble surface on the order of 100,000 ligands or more per microbubble.

In certain frequent embodiments, the functionalized microbubble has a diameter of between 50 nm to 100 μm.

Also, according to frequently included system and reagent embodiments, the functionalized microbubble comprises a coalescence-resistant surface membrane (e.g., gelatin), a filmogenic protein (e.g., albumin, gamma globulin, apotransferrin, hemoglobin, collagen, urease, human serum albumin, etc.), a filmogenic protein mixed with a polymer (e.g., albumin/dextran), a polymer material (natural or synthetic or modified), an elastic interfacial synthetic polymer membrane, a microparticulate biodegradable polyaldehyde, a microparticulate N-dicarboxylic acid derivative of a polyamino acid-polycyclic imide, a lipid, a protein, a surfactant, a phospholipid, a lipopeptide, a phosphatidylcholine, a stearic acid, a palmitic acid, a PEGylated ceramide, a PEGylated fatty acid, or a combination of two or more of the foregoing.

According to often included embodiments, the cell customization module is adapted to conduct cell modification using zinc finger nucleases (ZFN), transcription activator-like effector nucleases (TALEN), Clustered Regularly Interspaced Short Palindromic Repeats (CRISPR), CRISPR-associated (Cas) systems, lipid nanoparticles comprising mRNA, modified mRNAs (mmRNAs), small interfering RNA (siRNA), micro RNA (miRNA), antisense oligonucleotides, ribozymes, plasmids, immune-stimulating nucleic acids, antisense RNAs, antagomir, antimir, microRNA mimic, supermir, U1 adaptors, and/or aptamers.

Methods are also provided in the embodiments contemplated herein. In this regard, in certain frequent embodiments a method is provided for purifying a target cell from a patient blood sample in a closed-loop system, the method including connecting a parenteral inlet adapted to parenterally receive blood from the patient; permitting the blood to pass through the parenteral inlet to an apheresis or leukopheresis module to provide a sample containing a target cell; permitting the sample containing the target cell to pass through the parenteral inlet to a cell purification module; introducing a targeting reagent comprising a substrate bound to a targeting moiety to the blood from the patient, or fraction thereof, before or after the blood from the patient enters the cell purification module; permitting the targeting reagent to bind the target cell in the blood from the patient, or fraction thereof, to create a target cell/reagent complex in the cell purification module; separating the target cell/reagent complex from the blood from the patient, or fraction thereof; optionally separating the target cell from the targeting reagent to create a separated target cell; and returning the separated target cell to the patient via a parenteral outlet adapted to parenterally administer the separated target cell to the patient, wherein each of the steps occurs in the closed-loop system devoid manual intervention such that each step occurs without removing the blood from the patient or any component of the blood from the patient from the closed-loop system.

According to frequent embodiments of the methods contemplated herein, including for systems adapted to conduct such methods, the separated target cell comprises a plurality of separated target cells in a solution, and wherein the plurality of separated target cells are present in the solution at a concentration that is enriched for the target cell at least at or about 50% more than the target cell was present in the blood from the patient. Often, the plurality of separated target cells are present in the solution at a concentration that is enriched for the target cell between about 50% to about 90% more than the target cell was present in the blood from the patient.

According to frequent embodiments of the methods contemplated herein, including for systems adapted to conduct such methods, the targeting reagent is incubated with the blood from the patient, or fraction thereof, for between at or about 5 minutes to at or about 15 minutes.

Also often according to frequent embodiments of the methods contemplated herein, including for systems adapted to conduct such methods, the blood from the patient is permitted to pass from the parenteral inlet to an apheresis module or a leukopheresis module to remove non-nucleated cells and create the fraction thereof of the blood prior, and permitting the fraction thereof to pass to the cell purification module. Often, in frequent embodiments of the methods contemplated herein, including for systems adapted to conduct such methods, the separated target cell or the target cell/reagent complex is passed to a transfection module for cell modification to produce a modified cell prior to returning the modified cell to the patient via a parenteral outlet.

According to frequent embodiments of the methods contemplated herein, including for systems adapted to conduct such methods, the target cell/reagent complex is separated from the blood from the patient, or fraction thereof, using buoyancy, magnetic force, acoustic force, or electrophoretic force.

Also according to frequent embodiments of the methods contemplated herein, including for systems adapted to conduct such methods, each step of the recited steps occurs in a predefined time period. Often, in such embodiments the predefined time period is selected from the group consisting of: between at or about 5 minutes to at or about 30 minutes, between at or about 10 minutes to at or about 60 minutes, between at or about 15 minutes to at or about 90 minutes, between at or about 5 minutes to at or about 15 minutes, between at or about 10 minutes to at or about 45 minutes, between at or about 15 minutes to at or about 30 minutes, between at or about 20 minutes to at or about 45 minutes, and between at or about 5 minutes to at or about 90 minutes. Also often, the time period is at or about 10 minutes, at or about 15 minutes, at or about 20 minutes, at or about 25 minutes, at or about 30 minutes, at or about 35 minutes, at or about 40 minutes, at or about 45 minutes, at or about 50 minutes, at or about 55 minutes, or at or about 60 minutes, at or about 65 minutes, or at or about between 65 minutes and 90 minutes.

Also according to frequent embodiments of the methods contemplated herein, including for systems adapted to conduct such methods, each of the recited steps occurs in a total predefined time period. Often according to such embodiments the total predefined time period is selected from the group consisting of: between at or about 2 hours to at or about 6 hours, between at or about 2 hours to at or about 4 hours, between at or about 2 hours to at or about 3 hours, between at or about 3 hours to at or about 4 hours, between at or about 4 hours to at or about 5 hours, between at or about 5 hours to at or about 6 hours, and less than 2 hours. Also often, the total predefined time period is at or about 2 hours, at or about 2.25 hours, at or about 2.5 hours, at or about 2.75 hours, at or about 3 hours, at or about 3.25 hours, at or about 3.5 hours, at or about 3.75 hours, at or about 4 hours, at or about 4.25 hours, at or about 4.5 hours, at or about 4.75 hours, at or about 5 hours, at or about 5.25 hours, at or about 5.5 hours, at or about 5.75 hours, at or about 6 hours. Less frequently, the total predefined time period is greater than 6 hours for reasons noted herein.

Also according to frequent embodiments of the methods contemplated herein, including for systems adapted to conduct such methods, the closed-loop system or the sample is monitored in or between each recited step and determining if the closed-loop system is functioning properly and/or if the sample or the target cell meets a predetermined intermediate objective. Often in such embodiments, the condition where the sample is determined not to meet the predetermined intermediate objective, the sample is directed to undergo an additional processing until it meets the predetermined intermediate objective. In certain embodiments, the sample is directed to undergo an additional processing automatically and without human intervention.

According to often included embodiments, the introducing, permitting and separating steps comprises a two-step purification process, wherein non-target cells are separated from the target cell, and the target cell comprises a plurality of separated target cells in a solution, and wherein the plurality of separated target cells are present in the solution at a concentration that is enriched for the target cell at least at or about 50% more than the target cell was present in the blood from the patient.

In certain embodiments the targeting reagent is or comprises a microbead or microparticle, and the microbead or microparticle is separated from the target cell using a filtration system or a particle separation system to create the separated target cell. Frequently in such embodiments, the particle separation system comprises a magnetic particle separation system and the targeting reagent comprises a nanomagnetic particle. Often, the magnetic particle separation system comprises an electromagnetic chip adapted to include one or more individually addressable electromagnetic units.

Also, according to often included embodiments the targeting reagent is or comprises a microbubble, and the microbubble is separated from the target cell to create the separated target cell. Frequently the microbubble is separated from the target cell using one or more of applying overpressure, creating underpressure, ultrasonication, contact with a detergent, contact with a surfactant, through a pH change.

In often included embodiments, the target cell/reagent complex is separated from the blood or a processed component thereof in a solution by decantation, transfer from one syringe to another, skimming cell/reagent complexes from a layer of the solution, or introduction of the target cell/reagent complex to a two phase system comprised of immiscible low density fluid into which the microbubble/target component complexes will float.

Frequently, the microbubble is a functionalized microbubble comprising one or more reactive groups, linkers, ligands, or targeting moieties adapted for specific binding to a target cell. Often, the functionalized microbubble comprises a ligand present on the microbubble surface on the order of 100,000 ligands or more per microbubble. Also often, the functionalized microbubble has a diameter of between 50 nm to 100 μm.

According to frequent embodiments, the functionalized microbubble comprises a coalescence-resistant surface membrane (e.g., gelatin), a filmogenic protein (e.g., albumin, gamma globulin, apotransferrin, hemoglobin, collagen, urease, human serum albumin, etc.), a filmogenic protein mixed with a polymer (e.g., albumin/dextran), a polymer material (natural or synthetic or modified), an elastic interfacial synthetic polymer membrane, a microparticulate biodegradable polyaldehyde, a microparticulate N-dicarboxylic acid derivative of a polyamino acid-polycyclic imide, a lipid, a protein, a surfactant, a phospholipid, a lipopeptide, a phosphatidylcholine, a stearic acid, a palmitic acid, a PEGylated ceramide, a PEGylated fatty acid, or a combination of two or more of the foregoing.

Also according to frequently included methods, the cell modification comprises cell modification using zinc finger nucleases (ZFN), transcription activator-like effector nucleases (TALEN), Clustered Regularly Interspaced Short Palindromic Repeats (CRISPR), CRISPR-associated (Cas) systems, lipid nanoparticles comprising mRNA, modified mRNAs (mmRNAs), small interfering RNA (siRNA), micro RNA (miRNA), antisense oligonucleotides, ribozymes, plasmids, immune-stimulating nucleic acids, antisense RNAs, antagomir, antimir, microRNA mimic, supermir, U1 adaptors, and/or aptamers.

In certain embodiments of these aspects and all such aspects described herein, the purification module selects the modified cells using one or more parameters selected from cell size, cell shape, cell granularity, cell buoyancy, cell acoustics, and cell density.

In frequent embodiments a particle is incorporated in the kits and/or operation of the system with a sample, which particle becomes associated with a target cell in a predetermined manner, thereby altering a characteristic of the target cell or adding or incorporating a predetermined and identifiable and/or selectable characteristic to or with the target cell. In such examples a buoyant or magnetic particle may be bound to a cell. In frequent embodiments contemplated herein, an antibody or other binding moiety is used to facilitate the binding of the particle or increase the specificity of one or more cell types.

In some embodiments of these aspects and all such aspects described herein, the target cell is a nucleated blood cell selected from the lymphoid group consisting of B cells, T cells, activated or regulatory T cells, ]][ T cells, NKT cells, and natural killer (NK) cells.

All patents, patent applications, and publications mentioned herein, both supra and infra, are hereby incorporated by reference in their entireties.

BRIEF DESCRIPTION OF THE FIGURES

The skilled person in the art will understand that the drawings, described below, are for illustration purposes only. The drawings are incorporated in and constitute a part of this specification. The figures represent the unit operation used for cell purification and it is understood that this unit is in continuous, patient connected closed loop system.

FIG. 1 depicts an exemplary schematic and workflow diagram for a continuous flow microbubble module of the presently described systems.

DETAILED DESCRIPTION

Figure 2:
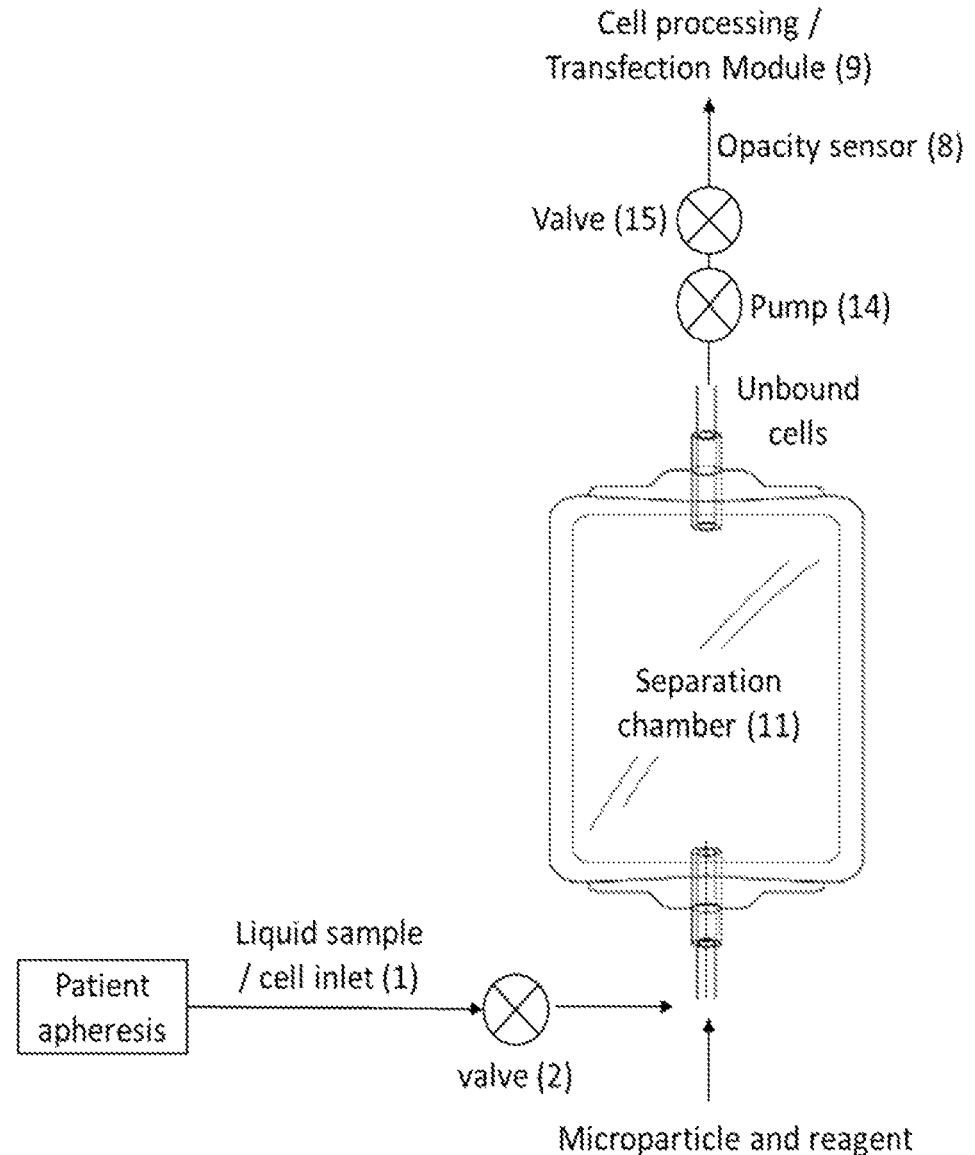
FIG. 2 depicts an exemplary schematic and workflow diagram for a continuous magnetic nanoparticle module of the presently described systems.

For clarity of disclosure, and not by way of limitation, the detailed description of the various embodiments is divided into certain subsections that follow.

Unless otherwise defined herein, scientific and technical terms used in connection with the present application shall have the meanings that are commonly understood by those of ordinary skill in the art to which this disclosure belongs. It should be understood that this disclosure is not limited to the particular methodology, protocols, and reagents, etc., described herein and as such can vary. The terminology used herein is for the purpose of describing particular embodiments only and is not intended to limit the scope of the present invention, which is defined solely by the claims. Definitions of common terms in immunology, and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, "closed-loop" refers to a system wherein at least a sub-population of cells is kept in a system that is a continuous flow-through, such that the cells are derived from the patient and can be modified and returned to the patient without being disconnected from the patient, nor disconnected from the patient in a manner that would require reintroduction of the cells to the patient.

As used herein, "continuous flow" refers to the flow of blood from a patient to the modular bedside system and back to the patient in which non-target cells, plasma and RBCs generally return to the patient whereas target cells can be customized by a customization module in the device and then returned to the patient; all in a closed-loop, patient-connected manner and in real-time. The term "continuous flow" does not exclude operations within a closed-loop system that occur while a cell population or sub-population is shunted or deposited for some period of time, into a holding, sampling or incubating chamber or receptacle within the system nor does it preclude batch collection or modification as long as the entire process remains patient connected and in a closed system.

"Discontinuous," as used herein, refers to not being part of a closed-loop such as a parenterally patient-connected closed-loop.

"Patient-connected" or "bedside" refers to when the system is connected to the patient and adaptations of the system permitting such connection, e.g., parenteral connection. Preferably, the patient can be connected to the system for the entire period of blood cell separation, enrichment, customization (if present), and purification. The blood flows from the patient to and through the system, including one or modules thereof (including an apheresis or leukopheresis module if present), and back to the patient. In such patient-connected or bedside systems, the patient remains connected with the same system through the entire procedure using the systems described herein, from obtaining the blood flow/sample into the described systems through the return of target cells (modified or otherwise) to the patient. This process and systems configured to conduct such processes are generally conducted in a manner that avoids avoid manual intervention after the patient is connected with the system.

As used herein, the term "consisting essentially of" refers to those elements for a given embodiment. The term permits the presence of elements that do not materially affect the basic and novel or functional characteristic(s) of that embodiment of the invention.

Other than in the operating examples, or where otherwise indicated, all numbers expressing quantities of ingredients or reaction conditions used herein should be understood as modified in all instances by the term "about."

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

As used herein, "treatment" means any way the symptoms of a condition, disorder or disease are ameliorated or otherwise beneficially altered.

As used herein, "patient" or "subject" often refers to an animal, including, but not limited to, a primate (e.g., human). The terms "subject" and "patient" are used interchangeably herein as an animal that is, was or could be parenterally connected with the systems described herein and/or that is, was or could be subjected to the methods described herein.

As used herein, "module" refers to system components that work together to achieve a functional outcome. In other words, components of a given "module" may or may not be in physical proximity and/or contact with each other, but, rather, are in "functional proximity," such that together they achieve one or more defined outcomes. A unit of the present systems may form a module.

As used herein, the term "sample" includes the terms "biological sample," "patient sample" or "subject sample" and refers to anything which may contain an target cell. The sample is or is derived from whole blood or plasma. Thus, as used herein a sample may be or contain a biological fluid or other reagent relevant to the systems described herein including, whole blood, fractionated blood, fractionated cells, plasma, serum, fluid, buffer or the like.

"Fluid sample" or "liquid sample" refers to a sample, as defined herein, containing or suspected of containing target cell, which material has sufficient fluidity to flow through a system contemplated herein. The fluid sample can be used as obtained directly from the patient or subject or following a processing step or steps that modify its character. Such samples can include human, animal or man-made samples. Typically, the sample is a liquid solution or biological fluid as described in more detail below. The fluid sample can be derived from any source, such as a physiological fluid, including blood, serum, plasma and the like. Processing may involve preparing plasma from blood, diluting viscous fluids, and the like. Methods of processing can involve filtration, distillation, separation, concentration, inactivation of interfering components, and/or the addition of reagents.

As used herein, "bubble" refers to a small and hollow globule such as a small spherical volume of gas enveloped or encased within a film (the film being non-limiting). Bubbles can be filled with any fluid that differs from the surrounding film, which most generally is a gas. A bubble is included within the definition of a "particle" as contemplated herein.

As used herein, "microbubbles" refer to small bubbles. Generally, microbubbles contemplated in the herein described embodiments are in the range of 0.5 µm to 20 µm in diameter. The sizes may be within or outside this diameter range as specifically recited herein. A microbubble is included within the definition of a "particle" or "micropar-ticle" as contemplated herein.

As used herein, "target cell" or "target cells" refers to a cell or cell population of interest in the systems and assays contemplated herein. A target cell is present in, suspected of being present in, isolated, purified, identified with, or otherwise derived from a biological sample. A target cell generally will maintain its status as a target cell regardless of its state of processing in the present systems, even if the target cell has different characteristics upon exiting a module compared with when it entered the module. A target cell, therefore, as used herein includes not only the specific target cell but also its progeny.

As used herein, "targeting moiety" refers to any molecule that is capable of specifically binding another molecule. In often included embodiments, the targeting moiety is an antibody or binding fragment thereof. In another embodiment, the targeting moiety is an antigen. In other embodiments of the invention, targeting moieties can include, without limitation: biological receptor molecules, such as the insulin receptor; ligands for receptors (e.g., insulin for the insulin receptor); and biological, chemical or other molecules that have affinity for another molecule, such as biotin and avidin. The targeting moieties of the present disclosure need not comprise an entire naturally occurring molecule but may consist of only a portion, fragment or subunit of a naturally or non-naturally occurring molecule, as for example the Fab fragment of an antibody. The targeting moiety may also include a marker, tag or label that can be detected. Targeting moieties may be generated by any method known in the art.

As used herein, "specifically binding," "specific binding" or "specifically binds" as used herein is refers to an antibody or other targeting moiety binds to a target such as an antigen, ligand or other analyte, with greater affinity than it binds to other molecules under the specified conditions of the present invention. In one embodiment the moiety would be an antibody or nanobody or portion of an antibody such as scFV. Natural ligands that bind specific cell receptors may also be employed. Often, "specifically binds" refers to binding of a targeting moiety (including a collection of targeting moieties on a microbubble, particle, or nanopar-ticle) with a target cell with a predetermined or known affinity. "Specifically binding," "specific binding" and "spe-cifically binds" is/are specifically contrasted with the "non-specifically binding," which is generally understood in the art or antibody and other targeting moieties. Targeting moieties may be attached to, included on, coated on, or otherwise chemically, electronically, magnetically, or physi-cally associated with a substrate by any means known in the art, including both direct covalent and non-covalent attach-ments and attachment via linker moieties or collections of moieties functioning effectively as linker moieties.

As used herein, "ligand" refers generally to a molecule that binds to a receptor, including the natural ligand for a target receptor.

A "bead," "microparticle" or "particle" is a structure of any shape and of any composition that is manipulatable or behaves according to predetermined principles (e.g., buoy-ancy or magnetic or acoustic) according to the systems and methods described herein. Such particles or microparticles can be comprised of any suitable material, such as glass or ceramics, and/or one or more polymers, such as, for example, nylon, polytetrafluoroethylene, polystyrene, polyacrylamide, sepharose, agarose, cellulose, cellulose derivatives, agarose or dextran, a metal, a metal alloy (e.g., FeO), lipid, protein, polymer, lipopeptide, gas/film, or other additional materials noted or contemplated herein. Examples of microparticles include, but are not limited to, bubbles, microbubbles, plastic particles, ceramic particles, carbon particles, polystyrene microbeads, glass beads, magnetic beads, hollow glass spheres, metal particles, metal alloy particles such as FeO containing particles, and other particles of complex compositions, microfabricated or micromachined particles, etc.

As used herein, the term "substrate" is intended to include a bead, a particle, a microparticle, and/or a microbubble, including combinations, sub-combinations, populations and sub-populations thereof. In one exemplary embodiment, a substrate comprises a microparticle coated or otherwise operably connected with a targeting moiety.

As used herein, "separation" refers to a process where a target cell of a sample is spatially separated from one or more other components of the sample. A separation can be performed such that one or more target cell populations is translocated to or retained in one or more areas of the system and at least some of the remaining sample components moved away from the area or areas where the target cells are translocated to and/or retained in, or in which the target cells are retained in one or more areas and at least some or the remaining components of the sample are removed from the area or areas. Alternatively, one or more target cells of a sample can be translocated to and/or retained in one or more areas and one or more sample components can be removed from the area or areas. It is also possible to cause one or more sample components to be translocated to one or more areas and the target cells of the sample to be translocated to one or more other areas. Separations can be achieved through, for example, filtration, or the use of physical, acoustic, chemical, electrical, or magnetic forces. Nonlimiting examples of forces that can be used in separations are buoyancy, gravity, mass flow, fluid dynamics such as counter flow (elutriation) dielectrophoretic forces, traveling-wave dielectrophoretic forces, and electromagnetic forces.

The terms "enriching" or "enriched" are used interchangeably herein and mean that the yield (fraction) of cells of one type, such as, for example, T cells, for use in the systems and methods described herein, is enriched to at least at or about 10%, at least at or about 20%, at least at or about 30%, at least at or about 40%, at least at or about 50%, at least at or about 60%, at least at or about 70% over the fraction of cells of that type in the starting sample. The enrichment of the target cell population can be adapted to enrich to a percentage purity and/or eliminate a particular target cell or cell types from the population.

As used herein, "isolating" or purification refers to separating a target cell type or types from a heterogenous mixture of cells such as would be in a leukapheresis output, such that preferably, 50%, at least at or about 55%, at least at or about 60%, at least at or about 65%, at least at or about 70%, at least at or about 75%, at least at or about 80%, at least at or about 85%, at least at or about 90%, at least at or about 95% over the fraction of cells of that type in the starting sample.

As used herein, "positive selection" refers to techniques that result in the isolation or enrichment of target cells, for example, cells expressing specific cell-surface markers.

As used herein, "negative selection" refers to techniques that result in the isolation or enrichment of non-target cells, for example, cells not expressing specific cell-surface markers.

A variety of cell separation and purification techniques are contemplated and described above and below. Though the specific techniques and reagents relevant to each manner of cell separation or purification are discussed in detail, the common theme for each technique/process/system is that it is integrated into the closed-loop, patient-connected bedside systems of the present disclosure. These systems are generally adapted for therapeutic or ameliorative purposes to transfect and transform target cells within the system and reintroduce those cells to the patient using the same system. As such, each of the embodiments herein are properly viewed though this lens. While specific aspects of each cell separation or purification technique are explored in somewhat isolation, each of these aspects is intended to be implemented in the embodiments of the present disclosure contemplating a closed-loop, patient-connected bedside therapy and/or therapeutic delivery system.

The techniques and systems contemplated in the present disclosure for cell separation and purification include at least filtration, leukapheresis, dielectrophoresis, fluorescence-activated cell sorting, magnetic-based separation/purification, buoyancy-based separation/purification, adhesion-based cell separation, ligand based binding, acoustophoresis, density purification, laser dissection, elutriation and other methods.

The present methods and systems contemplate an overarching requirement to not alter or harm the structure or function of the target cells that are purified in the purification module, nor adversely affect the medium in which they exist though that medium may be altered or replaced. Moreover, the present methods and systems are directed to increasing the specificity and speed with which target cells are separated/purified. In both regards, methods and systems employing surface protein-based target cell separation/purification techniques are often included and/or preferred. In such methods, a targeting moiety is utilized to specifically bind a cell surface protein on a known or predetermined cell population (including mixtures of cell populations sharing that cell surface protein). Often in such techniques a targeting moiety such as an antibody or binding fragment thereof is bound on or to a support (e.g., microbubble, magnetic particle, nanoparticle, bead, etc.) and the targeting moiety-bound support is introduced to a sample and permitted to mix within the sample and become bound with one or more target cells in the sample. Thereafter a process is used to separate or otherwise remove the support-bound cell from the remainder of the sample.

It is similarly included that the separation techniques utilized according to the methods and systems described herein are innocuous to the cells, and result in a usable yield, purity, and viability of isolated cells. In this regard, not all available separation technologies are suitable, and existing technologies require adaptations described herein to work according to the presently contemplated methods and systems. For example, a plurality of separation reagents have been developed for cell separation and purification. These include cell surface protein-based methods, DNA-based methods, gradient-based methods, appearance-based methods, among other techniques. Methods and apparatus using these separation methods are established. In general, however, existing methods suffer from a variety of drawbacks, including requirement for a specialized laboratory setting, batch requirements, inability for continuous processing, high cost in performance, low yields, long processing times, low specificity, damage to target cells, tainting of the cellular environment, safety of materials for introduction back to patient, and/or downstream target cell processing limitations due to the reagents and/or methods used in the separation.

The innovations of the present disclosure address these and other needs in the art and provide cell separation and purification techniques heretofore not possible in the context of a patient-connected, closed-loop, bedside setting.

During use of the systems described herein, a patient is coupled to the system in a closed loop fashion, with an inlet conduit coupled or connected to the patient to provide blood as input to the system. The inlet conduit receives blood directly from the circulation of the patient which is passed to the cell purification system. The cell separation module is designed, at a minimum, to perform collection of specific or known cell populations or collections present in the blood. This includes cell separation from blood components and optionally one or more enrichment steps. The cell purification systems contemplated herein are often adapted to purify cells from blood or other body fluids based on surface protein expression, size, shape, granularity, buoyancy, density, genetic identification, or any combination thereof. Mechanisms for cell separation/purification often according to the presently included methods and systems include buoyancy, centrifugal force, filtration, elutriation, sonic, electrical, magnetic, and/or acoustic properties.

In various embodiments, the systems described herein permit the purification of blood or other body fluid cells from a patient or subject, conduct optional other or additional steps or processes relative to these cells, and return of the cells to the patient in a closed loop format. This approach has benefits in terms of cost and reduced risk of contamination and supply chain issues, among a variety of other benefits.

The systems and approaches described herein can also involve one or more steps of cell selection to isolate or enrich for cells that have been modified in a connected system.

In some embodiments, the system can execute a program of cell purification in an automated manner with no or minimal operator input once the program is initiated.

In conjunction with any or all of the techniques described in further detail below, filtration is or can be used as a method of reducing the volume of samples and/or separating sample components based on their ability to flow through or be retained by the filter. Sample centrifugation and/or leukapheresis (or aspects thereof) may be part of this sample treatment. Filtration, sample centrifugation and/or leukapheresis (or aspects thereof) may occur before and/or after target cell separation/purification.

The presently contemplated purification systems and modules are often included in larger bedside systems for performing customized cell-based therapies and treatments in a patient-connected, closed-loop continuous-flow manner, including cellular modifications and treatments. In such systems blood is removed from a patient, processed, customized, and returned to the patient in a closed-loop, patient-connected manner. An arrangement of modules and units are provided in such systems that are sequentially used for separation and collection of target cells from whole blood, employing methods and systems described in detail herein, followed by one or more cell customization procedures such as transfection to produce modified cells, which modified cells are returned to the patient by means of an outlet conduit.

In the contemplated target cell transfection or cell transformation, once separated from whole blood, the nucleated blood cell population or enriched target cell population can be modified and/or customized using any method known in the art, including, without limitation, activation, expansion, induction of apoptosis, genetic manipulation, induction of antigen-specificity, etc. This can be achieved, for example, by the addition of cytokines, cross-linking specific receptors, addition of antigen, introduction of nucleic acid molecules (DNA, RNA, and/or modified versions thereof), protein agents, addition of drugs or small molecules, or any combination thereof.

A variety of cell customization agents can be applied to the target cell population in the different embodiments of the cell customization modules described herein. Cell customization agents, as used herein, include any molecule or compound capable of exerting a desired effect on a cell found in the blood. Non-limiting examples of cell customization agents include, but are not limited to, therapeutic nucleic acid molecules; peptide, protein, and polypeptide therapeutic agents, including, but not limited to polyclonal antibodies, monoclonal antibodies, antibody fragments; humanized antibodies, recombinant antibodies, recombinant human antibodies, fully human antibodies, cytokines, growth factors, apoptotic factors, differentiation-inducing factors, cell surface receptors and their ligands, and hormones; and small molecule agents, including small organic molecules or compounds. Non-limiting examples of classes of small molecule agents useful with the systems and methods described herein include anti-inflammatory compounds, antibiotics, antipyretics, vasodilators, anti-angiogenics, cytovascular agents, signal transduction inhibitors, and any combination thereof.

In some embodiments, the cell customization agent is an oncology drug, which may also be referred to as an anti-tumor drug, an anti-cancer drug, a tumor drug, an antineoplastic agent, a chemotherapeutic drug, or the like. In such embodiments, it is contemplated that systemic toxicity of chemotherapeutic drugs useful for, e.g., treatment of blood cancers such as leukemias, lymphomas or myelomas can be mitigated by administering the drug to nucleated blood cells, which will include the cancer cells, separated from whole blood, in a bedside, closed-loop system as described herein. Examples of oncology drugs that can be used in this manner include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litretinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs are ellipticin and ellipticin analogs or derivatives, epothilones, intracellular kinase inhibitors and camptothecins.

Cell customization agents can be therapeutically active themselves or they can be prodrugs, which become active upon further modification.

Therapeutic or cell-customizing or modifying nucleic acids include, but are not limited to, nucleic acids that encode one or more peptides or polypeptides of interest, such as mRNAs, modified mRNAs (mmRNAs), small interfering RNA (siRNA), micro RNA (miRNA), antisense oligonucleotides, ribozymes, plasmids, immune-stimulating nucleic acids, antisense RNAs, antagomir, antimir, microRNA mimic, supermir, U1 adaptors, and aptamers. In one set of contemplated target cell transfection or cell transformation embodiments, RNA comprised in a lipid nanoparticle is utilized to transform a target cell to generate target cells that produce a predetermined polypeptide or protein such as an antigen. Such target cell transfection or cell transformation is used, for example, in vaccine production for infectious disease, cancer, autoimmune disease, reproductive health, organ transplant, and/or allergen related disease.

SLIPSTREAM™ is another technique or platform/module useable in the presently contemplated systems. In such a technique or platform deep-primed T Cells are produced using an apheresis-based technique such as those described in, e.g., WO2019010222, WO2019010219, WO2019010224, each of which is incorporated herein by reference in its entirety. In a related exemplary embodiment, T Cells and monocytes are isolated. Monocytes are then matured into dendritic cells and used to prime the T cells with multiple tumor-associated antigens. In such embodiments, a blend of CD4 and CD8 cells is produced. The T cells then are expanded to produce several billion tumor-targeting-primed, high-viability CD4+ and CD8+ T cells. An agent such as an immune-stimulatory drug, is then tethered to the surface of the antigen-primed T cells, which are then returned to the patient.

Gene editing tools are included in the available cell customizations, including gene alterations, knockouts, or other changes to a cell's DNA, contemplated herein. For example, zinc finger nucleases (ZFN), transcription activator-like effector nucleases (TALEN), and Clustered Regularly Interspaced Short Palindromic Repeats (CRISPR) and CRISPR-associated (Cas) systems are frequently included gene editing tools included as cell customization options according to the methods, systems, and kits contemplated herein. See, e.g., Urnov et al. Nat Rev Genet. 2010; 11(9): 636-646; Kim et al., Genome Res. 2009; 19(7):1279-1288; Bogdanove & Voytas, Science 2011; 333(6051):1843-1846; Hockemeyer, Nat Biotechnol. 2011; 29(8):731-734; Kim et al., Nat Biotechnol. 2013; 31(3):251-258; Cong et al., Science 2013; 339(6121):819-823; Cho et al., Nat Biotechnol. 2013; 31(3):230-232; Genovese et al., Nature 2014; 510 (7504):235-240; Sebastiano et al., Stem Cells 2011; 29(11): 1717-1726, each of which is incorporated herein by reference in its entirety. Gene editing can be performed, for example, using a nuclease, including CRISPR associated proteins (Cas proteins, e.g., Cas9), ZFN, TALEN, and maganucleases.

With specific regard to CRISPR-Cas systems, a variety of reagents, methods techniques, and modules are utilized according to the present disclosure. For example, DNA breaks can be generated using a CRISPR-cas system, e.g., a type II CRISPR/cas system. Cas9 is an exemplary Cas enzyme used according to such methods disclosed, which catalyzes DNA cleavage. Enzymatic action by Cas9 can generate double stranded breaks at target site sequences which hybridize to at or about 20 nucleotides of a guide sequence and that have a protospacer-adjacent motif following the 20 nucleotides of the target sequence. A vector can be operably linked to an enzyme-coding sequence encoding a CRISPR enzyme, such as a Cas protein. Non-limiting examples of Cas proteins include Cas1, Cas1B, Cas2, Cas3, Cas4, Cas5, Cas5d, Cas5t, Cas5h, Cas5a, Cash, Cas7, Cas8, Cas9 (also known as Csn1 or Csx12), Cas10, Cmr1, Cmr3, Cmr4, Cmr5, Cmr6, Csa1, Csa2, Csa3, Csa4, Csa5, CsaX, Csb1, Csb2, Csb3, Csc1, Csc2, Csd1, Csd2, Cse1, Cse2, Cse3, Cse4, Cse5e, Csf1, Csf2, Csn1, Csn2, Csm1, Csm2, Csm3, Csm4, Csm5, Csm6, Csx17, Csx14, Csx10, Csx16, Csx3, Csx1, Csx1S, CsO, Csf4, Cst1, Cst2, Csh1, Csh2, Csy1, Csy2, Csy3, Csy4, including homologues or modified versions thereof. For example, a CRISPR enzyme can cleave of one or both strands at or around at least about 1, 2, 3, 4, 5, 6, 7, 8, 9, 10, 15, 20, 25, 50, 100, 200, 500, or more base pairs from a predetermined (e.g., first or last) nucleotide of a specific.

A vector that encodes a CRISPR enzyme comprising one or more nuclear localization sequences can be used. A CRISPR enzyme can comprise the nuclear localization sequences at or near the ammo-terminus, about or within a predetermined distance at or near the carboxy-terminus. CRISPR enzymes contemplated herein are non-limited.

The contemplated CRISPR/Cas systems can be used according to the contemplated customizations to perform site specific insertion or removals of sequence. For example, a nick on an insertion site in the genome can be made by CRISPR/cas to facilitate the insertion of a transgene at the insertion site. Alternatively, specific genes may be removed from the DNA of the cell. In often included embodiments, the presently contemplated cell customizations include methods of modulating the expression and/or activity of one or more target nucleic acid sequences in one or more cells by introducing into the cell one or more ribonucleic acid (RNA) sequences that comprise a portion that is complementary to each of the one or more target nucleic acid sequences and comprise a binding site for a CRISPR associated (Cas) protein; (ii) a Cas nucleic acid sequence or a variant thereof that encodes the Cas protein that targets but does not cleave the target nucleic acid sequence; and (iii) an effector domain. Such customizations may also include maintaining a target cell under conditions where these RNA sequences hybridize to a portion of the target nucleic acid sequences, the Cas protein binds to the RNA sequences and the effector domain modulates the expression and/or activity of the target nucleic acid, thereby modulating the expression and/or activity of the one or more target nucleic acid sequences in the cell. Exemplary CRISPR/Cas systems, methods, reagents, devices and modules contemplated herein are described, for example, in U.S. Pat. No. 10,253, 316; U.S. Patent App. Pub. Nos. 20160046961, 20160298096A1, 201662427325, 20170204407; PCT Application Pub No. WO2019067910A1, each of which is incorporated herein by reference in its entirety.

Regarding CAR T cell generation, it should be understood that substantially any CAR polypeptide that can be used in conventional CAR T therapy can be employed or introduced in the systems and methods described herein. That is, the specifics of the CAR are not generally critical to the invention described herein. That said, for the avoidance of doubt, the following describes options and considerations for a range of CAR constructs that can be used with the systems and methods described herein.

Figure 4:
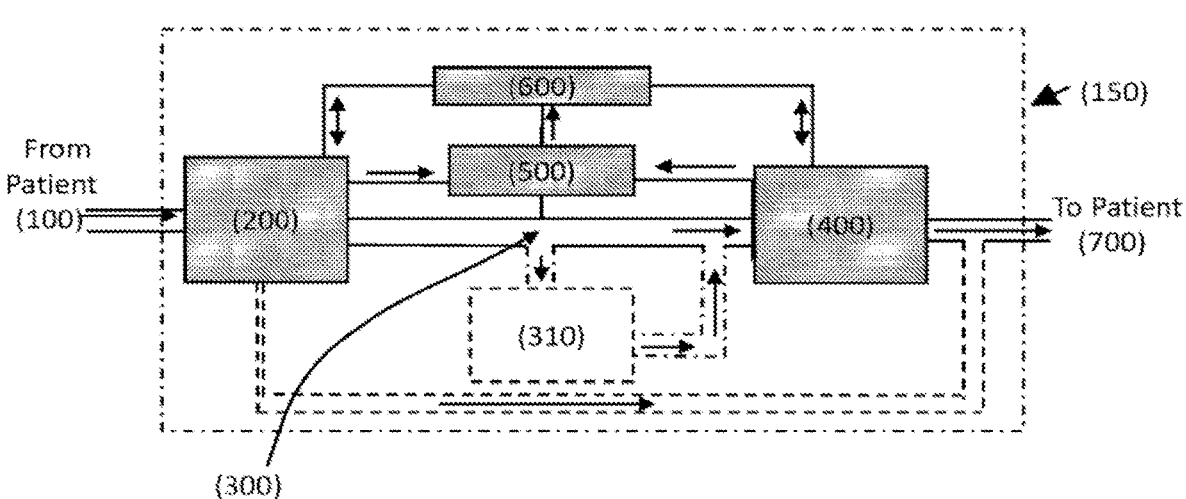
FIG. 4 depicts a schematic of an exemplary embodiment of a system for cell customization and modification incorporating the cell purification modules described herein.

In one aspect, as depicted in FIG. 4, a system (150) as described herein may include an inlet conduit/tubing (100) to receive blood, whether whole blood or whole blood that has been subject to leukapheresis or apheresis, from a subject or patient, connected to a cell purification module (200) that separates or enriches one or more desired subset (s) of nucleated blood cells, optionally washes and concentrates them or exchanges their medium for one better-suited for cell modification. The wash may include systems to specifically remove materials used in the purification module for reasons related to patient safety. The cell purification module (200) is connected via a conduit or tubing (300) to an optional cell customization module (400), within which cells are customized by the introduction of one or more customization or modifying agents. Customized cells flow (via action of a pump or other mechanism suitable in the art) from the cell customization module (400) to the patient via outlet conduit or tubing (700). The cell purification module (200) is also connected in this embodiment to conduit or tubing (150), within which plasma, non-nucleated cells or other non-target cells, are returned to the subject through a conduit or tubing (700). The outlet conduit or tubing (700) can include a valve or port that permits flow-through of a blood fraction comprising that blood portion or portions that are not transmitted to the cell customization module, e.g., plasma, non-nucleated cells or other non-target cells, back to the patient or subject, while the customized cells are reintroduced to the patient or subject separately after the customization steps are completed. A system as described herein also includes at least one detector (500) that interfaces with one or more of the cell purification module (200), cell customization module (400), or a component thereof as described herein. A detector can detect, via an appropriate sensor, for example, the number of cells or some property of the cells or medium indicative of, for example, cell status, cell viability, cell modification or customization, etc. In certain embodiments, there are a plurality of detectors (500) or sensors that detect various properties, at various points within the system to provide information to a processor (600) that controls the system and its various modules. The processor (600) is connected to each of the cell purification module (200), the cell customization module (400), and to the various components of these, as well as any pump(s), valves, or other components requiring control within the system.

In frequently included embodiments, the entire process depicted in FIG. 4, and described above is completed within or less than 4 hours, and the subject or patient remains connected to at least one of the inlet conduit (including connection through a leukapheresis or apheresis module/step) and/or the outlet conduit/tubing during the entire process. In certain embodiments, the entire process depicted in FIG. 4, and described above is completed between about 2 hours to 4 hours. Also in certain embodiments, the entire process depicted in FIG. 4, and described above is completed within or less than 6 hours. As such, the function of each the purification module and cell customization module are constrained by a time limitation defined by a balance of the preferred time for the overall procedure and the relative time it takes to complete a predetermined level or status of the processing of each module.

Regarding timing, that is an important aspect of the overall purpose of the system. As the system is parenterally patient connected, it is important that the time the system is parenterally connected with the patient be kept within tolerance periods. All contemplated system embodiments herein are configured with this aspect in mind. Tolerance to prolonged connection with the system is understood to be variable, with an understanding of the present inventors that reducing this total time period and maximizing the effectiveness of the present systems within that time period results in inter-module cycle time period reductions and better tolerance of the patients/subjects to the treatment protocol delivered by the systems. As such the present systems are configured to operate within strict cycle times. This configuration relates to the purification technologies and modules utilized, the detector mechanisms and functionalities, the disposable aspects of the system, reagents, software, and/or the structural and/or functional arrangement of the system to ensure efficient and safe operation and quick passage of blood/sample/target cells within the systems and between or within modules. Overall, a treatment protocol, beginning with the presently described closed-loop parenteral connection of the patient with the system and ending with removal of the parenteral connection from the patent, will last between 2 to 6 hours. Most frequently this time period is between 2 to 4 hours. Within these ranges there are subranges as contemplated in the embodiments of the present systems and their operation. These ranges may be anywhere in the range of at or about 2 hours, at or about 2.5 hours, at or about 3 hours, at or about 3.5 hours, at or about 4 hours, at or about 4.5 hours, at or about 5 hours, at or about 5.5 hours, at or about 6 hours, or shorter than 2 hours. In certain limited embodiments the time period may be above 6 hours. It is noted that there are a variety of patient safety issues that are balanced in the process of the automated manner the present systems are configured and how they operate. In this regard, timing and safety considerations are balanced to ensure not only that the proper or desired treatment is provided in a quick and efficient manner, but also that safety protocols are rigorously adhered to in the system to ensure that no harm is caused by the operation of the system. Such issues related to the safety of modules, sample processing procedures, and reagents are discussed herein and integrated in the most frequent embodiments.

While a variety of cell purification methods and systems are contemplated herein, it is appreciated by the inventors that not all available cell purifications are suitable for the patient-connected systems of the present disclosure. For example, fluorescence-activated cell sorting, laser capture microdissection, methods dependent on cell culture and differentiation, methods dependent on incubation of cells with other cells or materials that are or could be harmful to the patient, methods dependent on attachment to biomaterials such as fibronectin, among other related and similar methods having similar or related drawbacks are not contemplated as part of the systems and apparatus disclosed herein.

Further, the presently contemplated systems and methods employ cell purification methods and systems that permit immediate passage of "processed cells" (i.e., target cell populations that have bene purified from non-target cells or other blood components) to a cell customization module or the next step or module in the system. In this regard and simply as one example, conventional DYNAL® (Dynal, A.S., Oslo, Norway) bead-based methods are not suitable in the present methods and systems. For example, such conventional DYNAL bead-based methods and reagents require incubation with target cells over a prolonged period such as multiple days. Eventually, after this prolonged time period or an additional time period, the Dyna beads detach from the target cells. Transduction of the target cells is not possible until after the beads detach from the target cells, thus prolonging the process and rendering a patient connected system employing such methods and reagents unsuitable and not previously possible. While DYNAL beads are specifically discussed, the concept of research lab tools, which tools require long time periods (e.g., hours to days) to process, being unsuitable for the presently described systems and methods is intended to be a general statement. This holds true with regard to these or other conventional beads that require a prolonged time period of incubation, or non-biocompatible or harmful reagents, for connection with a target cell. This also holds true with regard to these or other conventional beads that require a prolonged time period of incubation/waiting, non-biocompatible or harmful reagents, or cell viability or function disruptive methods or reagents, for detachment from a target cell. Each of these methods and reagents is considered to fall outside the presently contemplated embodiments as not compatible with the contemplated patient-connected (including closed-loop) systems.

Blood from a patient into the presently contemplated systems is typically received in an apheresis unit or module or leukapheresis module or unit prior to purification. A variety of apheresis or leukapheresis technologies and devices may be employed. For example, non-limiting examples of currently used apheresis devices include, for example: COBE® Spectra, TRIMA®, and SPECTRA OPTIA® systems (all marketed by Gambro BCT) and the AMICUS™ and CS_3000+™ and Amicore™ (marketed by Fenwal/Baxter) devices.

In various embodiments, a cell washing unit can be integrated with the presently described systems, for example, placed between an apheresis module and the cell purification module and/or after the cell purification module, to remove one or more components of a cell suspension produced by the apheresis module or cell purification module, or in order to place the cells into a medium or solution better conducive to cell enrichment procedure. A cell washing unit generally includes a source of cell wash solution, such as a reservoir or bag of wash solution, connected via conduit or tubing to the washing unit. The flow of cell wash solution can be controlled by a valve controlled by a processor. A cell washing unit can include a centrifugal unit similar to the centrifugal unit in an apheresis device; cells enter the washing unit, are mixed with wash solution introduced from a reservoir or other source of wash solution via conduit connected to the washing unit, and the suspension is spun to concentrate cells. One or more rounds of cell washing and re-suspension can be performed before the cells pass out of the cell washing unit. A cell washing unit can be interfaced with a detector configured to detect one or more properties of the cells or cell suspension, e.g., cell number, solution density, solution pH, solution ionic strength, etc.

Other stand-alone devices, such as the Gambro COBE 2991™ Blood Cell Processor or the Fresenius Kabi Lovo™ or Baxter CYTOMATE™ or elutriation devices such as Rotea™ marketed by ThermoFisher. Cell Washing System are often used to wash, concentrate, or place cells into appropriate concentration and medium prior to purification. Devices of this kind can be adapted for or integrated into a system as described herein for bedside customization of nucleated blood cells.

Microbubbles coupled to a targeting moiety such as a protein, peptide, oligonucleotide, carbohydrate, ion exchange material, metal binding moiety or low molecular weight receptor agonist or antagonist are used to concentrate and purify cells of interest from a crude biological sample such as blood, other body fluid or biological sample. After removal of the microbubbles/targeting moiety, the cells of interest are separated from any remaining microbubbles by known or specified techniques.

The cell purification system often advantageously utilizes microbubble separation of target cells or one or more cell population from other blood or sample components. For example, highly efficient component separation may be achieved using flotation methods involving binding target cells with encapsulated gas microbubbles. The efficiency of such separations is enhanced by the substantial density difference between gas microbubbles and liquid sample media, so that the process is capable of high sensitivity. Flotation separations inherently proceed more gently than magnetic separations and the gas microbubbles advantageously are prepared using flexible encapsulating materials, so that the possibility of causing damage to sensitive target components such as cells during separation may thus be minimized. Unlike some magnetic systems such as DYNAL, MBs can be made from biomaterials that are safe for re-administration back to patients which is critical for patient connected systems. DYNAL and other bead systems used in centralized manufacturing have the time and mechanisms to ensure 100% removal of the beads prior to final formulation that is delivered back to the patient which is not possible in a patient connected manner. Microbubbles also permits easy removal of the microbubbles from the target cell after its use is complete, for example by bursting the microbubbles. Therefore, a process for the separation of target material from a liquid sample is provided that includes coupling a target cell to a microbubble, allowing the bound microbubble to rise in the surrounding fluid optionally to a specific area, and then removing the microbubble from the target cell (positive selection) or recovering target-free sample material (negative selection) of the cells that were not bound to the targeting MBs.

The process of incubating cells with microbubbles and mixing/agitating the combined cells with microbubbles to provide for attachment of the microbubbles with cells is generally defined by a predetermined time duration, for example, between at or about 5 minutes to at or about 15 minutes. This timeframe is critical as much longer are not possible in patient connected systems. In certain often included embodiments, the incubation and/or agitation time is less than at or about 15 minutes. In certain embodiments, the incubation and/or agitation time is greater than at or about 15 minutes. In certain embodiments, the incubation and/or agitation time is less than at or about 10 minutes. In certain embodiments, the incubation and/or agitation time is less than at or about 5 minutes. In certain embodiments, the incubation and/or agitation time is between at or about 5 minutes to at or about 10 minutes.

The process of incubating cells with microbubbles and mixing/agitating the combined cells with microbubbles to provide for attachment of the microbubbles with cells is generally defined by a predetermined temperature, for example, between at or about 0° C. to at or about 40° C. In certain often included embodiments, the incubation and/or agitation temperature is between at or about 10° C. to at or about 30° C. In certain embodiments, the incubation and/or agitation temperature is between at or about 15° C. to at or about 25° C. These temperature ranges are often preferred in patient connected systems.

Microbubbles that are useful in accordance with the present systems and methods include any microbubbles that can be prepared in a targetable form. In general, in the present systems and methods, the encapsulating material and gas content are both biocompatible.

Microbubble encapsulating materials (or shell material) suitable for buoyancy-based separation is generally composed of biocompatible and bioinert materials. This includes being inert relative to the target cells, and any contamination that results does not affect downstream system processes or have an in vivo effect when passed back into a patient in the closed loop. In this regard, the anionic lipid phosphatidylserine is often avoided. Moreover, other lipids commonly taught in the context of microbubble shell (for example, phosphatidic acids, phosphatidylinositol, cardiolipins, sphingomyelins), which participate in cell signaling, are on the less preferred list of encapsulation materials.

Representative examples of encapsulating materials include a coalescence-resistant surface membrane (e.g., gelatin), a filmogenic protein (e.g., albumin, gamma globulin, apotransferrin, hemoglobin, collagen, urease, human serum albumin, etc.), a filmogenic protein mixed with a polymer (e.g., albumin/dextran), a polymer material (natural or synthetic or modified), an elastic interfacial synthetic polymer membrane, a microparticulate biodegradable polyaldehyde, a microparticulate N-dicarboxylic acid derivative of a polyamino acid-polycyclic imide, a lipid, a protein, or a surfactant. The encapsulating material may be a phospholipid and/or a lipopeptide.

Exemplary shell forming lipids that present no net charge and may be utilized include phosphatidylcholines, in particular disteroylphosphatidylcholine, dipalmitoylphosphatidylcholine, and dimyrstylphosphatidylcholine), disteroylphosphatidylethanolamines, fatty acids, in particular stearic acid and palmitic acid, PEGylated ceramides, and PEGylated fatty acids. Often the microbubbles contain polypeptides, including a specific peptide, polypeptide, protein or combinations thereof (including multiple different types of each category). Synthetic and naturally occurring peptides, polypeptides, proteins or combinations thereof are contemplated.

Lipopeptides which may be used include lipid-substituted peptide moieties which are amphiphilic and capable of membrane formation. Such lipopeptides may be formed from individual peptide units, for example, comprising from 2 to 50 amino acid residues and each often carrying one or more lipophilic hydrocarbon chains containing between 5 and about 50 carbon atoms. The number of amino acid residues in the individual peptide units is often below 20, or below 10, or between 2 and 8. The peptide units may also comprise alternating hydrophobic and hydrophilic amino acid residues such as alanyl and diaminopropionyl, and may comprise one or more complementary sequences and/or a targeting sequence with affinity for biological receptors. Optionally, residues of charged amino acids such as lysine and glutamic acid can be selected to provide side-chain functionalities such as enhanced stabilization comprising positively and/or negatively charged groups respectively at neutral pH. The lipid component of the lipopeptides often comprises an alkyl, alkenyl or alkynyl chain, especially an alkyl chain. Such chains often contain between 5 and 25 carbon atoms and can be prepared from, for example, fatty acid derivatives. Suitable fatty acids include oleic acid, stearic acid, palmitic acid and the like. The number of hydrocarbon chains per individual lipopetide unit may vary depending on the number of residues present.

Microbubbles bearing a surface charge may be utilized. Such microbubbles may offer enhanced stability and dispersibility, and resist coalescence. Such microbubbles may permit the reduction or avoidance of stabilization reagents. For example, microbubbles may be stabilized by a fluid filmogenic coating, for example, to prevent coalescence and to provide an interface for binding of molecules to the microbubbles.

Membrane-forming amphiphilic encapsulating materials such as phospholipids and lipopeptides may be included at the microbubble-sample liquid interfaces as monolayers, bilayers or multilayers.

Microbubbles are frequently formed by the introduction of a gas into a solution of protein, for example, by sonication or other mechanical treatment in the presence of a fluid such as a gas or a gas mixture. Heating a solution of protein may also be used. Microbubbles may require stabilization, which can be accomplished by routine methods, including via denaturation of the protein forming the bubble and/or treatment with Cr+++. In one aspect, the microbubbles are stabilized by cross linking with aldehydes such as glutaraldehyde or formaldehyde.

In another embodiment of the invention, the microbubbles are glass microbubbles. In one aspect of the invention, the glass microbubbles have a density of about 0.6 g/cc and an average diameter of about 30 μm. In related embodiments, the microbubbles are borosilicate glass such as those supplied by 3M™. Borosilicate glass bubbles can be treated with sodium hydroxide to expose a silica surface and then reacted with a silanating agent such as an 3-amino-propyl-triethoxy silane, creating a surface coated with a primary amines. The microbubble can then be reacted with NHS-biotin to form a biotinylated glass microbubble, which can then be coated with streptavidin, if desired. This streptavidin microbubble can then be easily coated with a biotinylated ligand such as a biotinylated antibody; alternatively epoxy coated glass micro bubbles can be reacted directly with ligands or coated directly or indirectly by methods known to those skilled in the art.

Microbubbles are often formed via the introduction of a gas into a solution of protein, for example, by sonication. The bubbles can be filled with any gas, including, but not limited to oxygen, nitrogen, carbon dioxide, helium, fluorocarbon gases and various combinations thereof, such as air.

Regarding fluid used to fill the microbubbles, biocompatible substances, including mixtures, which are at least partially in gaseous or vapor form at processing temperatures can be used as the microbubble fluid.

The size of microbubbles used in the process of the invention may vary depending on, for example, parameters such as the nature and size of the target to be isolated. Any microbubble which, when bound to the target, is less dense than the liquid medium of the sample may be suitable.

Often a diameter of a microbubble within a population of microbubbles has a diameter of between 50 nm to 100 μm, and often between 200 nm and 25 μm. In certain embodiments, the microbubbles are generally in the range of 0.1 to 100 microns, typically 1 to 50, and frequently 1 to 20 or 1 to 10 microns in diameter. Often such populations of microbubbles have similar characteristics across the population, such as a uniform or relatively uniform diameter in the noted ranges.

The microbubbles may conveniently be of similar size to the targeted cells. In one related example, microbubbles within a population of microbubbles have a diameter of between 1 to 10 μm, or between 3 to 5 μm.

The number of microbubbles utilized in the present systems to isolate a particular cell from a sample will vary depending on factors such as the natures of the microbubbles and the target, and the number of other components present in the sample. In general, simple experimentation may be carried out to determine optimum microbubble:targeted component number ratios for particular separation systems in order to ensure flotation of the microbubble/targeted component complexes. At a more specific level the number of microbubbles required may also depend on the content of target component relative to non-target components in a sample; thus, for example, samples containing a low proportion of target component may require treatment with a relatively large number of microbubbles to ensure adequate separation.

The strength of the bond between the microbubble and the target cell is an important parameter in buoyancy-based cell separation. This bond strength is controlled by both the affinity and the avidity of the target cell:targeting moiety pair. Therefore, it is often desired to select a ligand with high affinity to the target in addition to being highly specific for the target. Targeting moiety density often comes into play in this setting as well since it is important to have a high enough density that if a target cell contacts the microbubble, it will become bound in a short time period. And, that when bound, it binds with high affinity. The density of the ligand on the microbubble, therefore, is often adapted so that the number of target:ligand bonds is sufficient to resist detachment of the cell from the microbubble during the buoyancy-based separation procedure. Microbubbles that resist or at least do not easily aggregate by at all, let alone based on the nature of the targeting moiety. Thus, targeting moiety densities will often be tailored to have a balance between binding affinity and avoiding aggregation.

Non-specific binding of microbubbles to non-targeted is also less preferred, though this potential increased with heightened targeting moiety density, particularly in the case of antibody-based targeting moieties. Antibody densities on the order of 100,000 molecules per microbubble, or between 60,000 to 200,000 per microbubble, are often preferred. In certain embodiments, however, antibody density of between 300,000 to 800,000 per microbubble are utilized.

Targeting moiety density is based on density of the anchor in the shell for the targeting moiety. Representative anchors include lipids and other hydrophobic molecules bearing one or more functional groups for bioconjugation of the targeting ligand, for example, including separate hydrophobic, hydrophilic, and conjugation portions, discussed herein. Examples of hydrophobic moieties suitable for use as the anchor of present disclosure include branched and unbranched alkyl chains, cyclic compounds, aromatic residues and fused aromatic and non-aromatic cyclic systems. In some instances the hydrophobic moiety will consist of a steroid, such as cholesterol or a related compound. Preferred species include lipids, steroids, and hydrophobic polyamino acids. Alternatively, or in addition, anchors in which the hydrophilic portion comprises a polymer chain are included. In a such embodiments, the polymer chain is often poly-enthyleneglycol (PEG). In one embodiment the average molecular weight of the PEG is between 500-5,000. In another often-included embodiment, the average molecular weight of the PEG is between 1,000-4,000.

The density of the anchor can be expressed as percent by moles of the anchor relative to the total shell-forming materials. The relationship between anchor density and targeting moiety density may be empirically determined for a given targeting moiety and conjugation chemistry by synthesizing microbubbles bearing increasing density of anchor, reacting with excess ligand, removing unconjugated targeting moiety, and measuring the density of conjugated targeting moiety on the microbubbles. Exemplary methods for measurement of targeting moiety density include ELISA and radio-labelling of the targeting moiety and gamma counting. Often, an anchor density of between 1-20% is utilized. Often the anchor density is between 2% to 10%. In certain embodiments, the anchor density is below 2%.

Anchor detachment from the microbubble shell is often desired. This is avoided or reduced through the use of an anchor firmly bound within microbubble shell via short range attractive forces between the hydrophobic portion of the anchor and hydrophobic tails of adjacent shell-forming lipids. The anchor is often selected to optimize the strength of these attractive forces for a specific shell composition material. This can be achieved, for example in the case of lipophilic hydrocarbon chains, by selecting species with a sufficient number of carbon atoms to form a sufficient number of bonds with adjacent shell lipids. Preferred compositions include between 14 and 24 carbon atoms. Often compositions comprise between 16 and 20 carbon atoms. The number of lipophilic chains can be varied, and will often comprise one or two hydrocarbon chains.

In order to render them targetable, the microbubbles used in accordance with the invention may be coupled to one or more appropriate targeting moieties, e.g. chelating moieties, affinity ligands or vectors, either directly or through appropriate linking groups. In certain instances, however, the microbubble membranes may themselves have affinity for a target component and thus may be regarded as combined membranes and targeting moieties. Thus it has been found that such microbubbles, when added to a population of murine bone marrow cells devoid of differentiated cells (i.e. so-called lineage negative cells), bind to and float a subpopulation which comprises less than 5% of the lineage negative cells but contains almost 100% of the in vitro colony forming cells.

In the separation of biological components, the microbubbles may, for example, be directly coupled to vectors such as monoclonal antibodies which recognize specific target components. Alternatively, the microbubbles may be coupled or linked to a peptide or a secondary antibody which has specificity for a primary antibody which in turn has specificity for the target components. Such use of secondary antibodies is advantageous in that appropriate selection of a secondary antibody allows the preparation of "universal" microbubbles which may be used for a wide range of applications since the primary antibody can be tailored to the particular target components.

The microbubbles may also be coupled or linked to substances such as streptavidin/avidin to allow biotinylated vectors to be coupled, or may be coupled or linked to vectors such as proteins, lectins, polysaccharides, peptides, nucleotides, carbohydrates, low molecular weight receptor agonists or antagonists.

Functionalized microbubbles carrying one or more reactive groups may be employed in the present systems for binding to receptor molecules located on cell surfaces. Microbubbles comprising a thiol moiety, for example, may bind to cell surface receptors via disulphide exchange reactions. The reversible nature of such reactions means that coupling and subsequent detachment may be controlled by altering the redox environment. Similarly, functionalized microbubbles with membranes comprising activated esters such as N-hydroxysuccinimide esters may be used to react with amino groups found on a variety of cell surface molecules.

The targeting moiety may be directly anchored to the microbubble, for example, by using a heterobifunctional reagent such as sulfosuccinimidyl 4-(N-maleimidomethyl) cyclohexane-1-carboxylate. Alternatively or in addition, the targeting moiety is indirectly anchored to the microbubble, such as through the interaction of at least one other molecule (e.g., coupling streptavidin to the microbubble and targeting moiety is biotinylated, such that the streptavidin and biotin interact to couple the targeting moiety to the microbubble.

In the case of glass microbubbles, these are less preferable but can be treated to generate reactive surface residues, which are reacted with 3-aminopropyltriethoxy silane to generate amines. In another aspect, glass microbubbles are cis-diol coated and the targeting moiety is directly coupled to the glass through the cis-diol coating. The cis-diol coating can be generated, for example, by treating the glass microbubbles to generate reactive surface hydroxyl residues, reacting the hydroxyl residues with 3-glycidoxypropylt-rimethoxysilane to generate epoxy functional residues, and treating the epoxy functional residues with acid to convert the epoxy function to cis-diol functions. Coupling of a microbubble to a desired targeting moiety may be achieved by covalent or non-covalent means, for example involving interaction with one or more functional groups located on the microbubble and/or vector. Examples of chemically reactive functional groups which may be employed for this purpose include amino, hydroxyl, sulfhydryl, carboxyl, and carbonyl groups, as well as carbohydrate groups, vicinal diols, thioethers, 2-aminoalcohols, 2-aminothiols, guanidi-nyl groups, imidazolyl groups and phenolic groups. The vector and microbubble may also be linked via a linking group; many such groups are well known in the art. Connection of the vector and microbubble, optionally via a linker, may therefore be readily achieved using routine techniques.

While targeting moieties are discussed in detail in connection with microbubbles, the described targeting moieties may be adapted for use with beads and particles (including nanoparticles) described and contemplated herein. Thus, while the above section is set forth under the Microbubble heading it is intended for exemplary purposes only, and one of skill in the art would appreciate the transferable applicability of this section to other supports beyond microbubbles, such as buoyant beads and particles and magnetic particles and magnetic nanoparticles.

An optional specific step of collecting a population of cell-bound microbubble complexes may be provided in the present system. This population may be removed from the sample, for example, by decantation, transfer from one syringe to another, or by simply skimming off the floating microbubble layer. If desired the separation may be enhanced by overlaying the sample with an immiscible low density fluid into which the microbubble/target component complexes will float, thereby totally separating them from the sample; two phase systems comprising immiscible aque-ous layers with different densities, for example two phase dextran-polyethylene glycol-water systems.

In certain embodiments, the liquid containing the microbubbles may be centrifuged or subjected to a bubble trap to further effect the separation more rapidly.

Other microbubble removal techniques which may be employed, e.g. when using gas microbubbles that are rela-tively resistant to bursting, include uncoupling/detaching the microbubbles by, for example, hydrolysis, pH change, salt addition, change in redox environment, enzymatic cleavage, among other methods.

While complex separation is discussed in detail in connection with microbubbles, the described separation tech-nologies may be adapted for use with beads and particles (including nanoparticles) described and contemplated herein. Thus, while this section is set forth under the Microbubble heading it is intended for exemplary purposes only, and one of skill in the art would appreciate the transferable applicability of this section to other supports beyond microbubbles, such as buoyant beads and particles and magnetic particles and magnetic nanoparticles.

Following separation, microbubble removal may, for example, be effected by collapse or bursting of the microbubbles. Collapse refers to reducing or eliminating the buoyancy of the microbubble, and an alteration of the physical structure of the microbubble shell materials. Microbubble collapse renders the cells no longer buoyant, allowing them to be concentrated, buffer exchanged, and pipetted using standard laboratory methods. Collapse of the microbubble also permits sequential separation. After col-lapse the shell material is removed from the cells and may be done so rapidly. It is often included that microbubble collapse occurs within a known amount of time, such as within 10 seconds or below.

Application of an overpressure or under pressure, by ultrasonication, adding a small amount of a detergent or surfactant, or otherwise by a suitable pH change may be employed. It will be appreciated that the microbubble burst-ing conditions should be sufficiently mild to avoid damaging the bound cells. Often, this procedure does not expose the bound cells to adverse conditions or otherwise alter the cells in manner detrimental to their further processing or use. For example, reduction in viability, alteration in cell surface proteins, alteration in transcription, and/or alteration in activation state due to the cell separation procedure is/are generally avoided. In certain embodiments, microbubble collapse is achieved under conditions compatible with bio-logical substances, including cells, proteins, nucleic acids, and other biomolecules. Often, collapse is achieved at physiological pH. Also often, collapse is achieved at tem-peratures between 2-39 degrees C., in an isotonic medium, and/or without the use of detergents or reagents that may alter cell membrane integrity or cellular homeostasis.

Methods requiring changes in salt content, pH, or tem-perature beyond physiologically tolerable levels are avoided, as are the use of detergents, enzymes, and hydro-lysis. Further, the use of ultrasound at high mechanical index is generally avoided in the cell purification module.

It has been demonstrated that brief heightened pressures of up to 2-4 atmospheres may be used to burst microbubbles without harming bound cells.

One useful method for applying a specific overpressure or under pressure is via syringe use combining a volume of sample and a volume of air or other gas and closing the syringe. The plunger is then operated to apply variable over pressure or under pressure at a constant temperature. A vacuum chamber may also be employed to achieve the desired pressure levels.

Another useful method involves diffusion of the gas microbubble core through the shell. This can be achieved, for example, by immersing the cell-microbubble complexes into a buffer in which the partial pressure of the encapsulated gas is essentially zero to create a gradient across the shell of the microbubble, leading to collapse of the microbubble. In general according to the present disclosure, the contents of the gas core of the microbubble is often selected to provide for efficient microbubble collapse.

Following microbubble removal by bursting, a proportion of microbubble-encapsulating material may remain attached to the separated target cell. This material is importantly not of a size, concentration or character that affects cell viability. The remainder of the prior encapsulating material may be removed by, for example, washing procedures.

Often the degree of residual shell attached to the targeted cell is modulated by the selected shell materials and/or the collapse procedure. Often, it is desirable for the microbubble shell to take the form of multiple sub-micron particles after collapse. Though not bound to any particular theory of operation, the structure that the collapsed microbubble shell forms may be related to the physical phase of the lipids during the collapse procedure. In this regard, the inclusion of shell forming lipids that are predominantly in the liquid expanded phase during the collapse procedure are often utilized. Upon collapse, lipids predominantly in the liquid expanded phase tend to associate into structures of less than 1 micron in the longest dimension. In contrast, lipids that are in the condensed phase during the collapse procedure tend to form tubes, folds, sheets, and other large (1 um or greater) structures. Heating the microbubble:cell solution past the main transition temperature of the lipid is often used to provide lipids in the liquid expanded form.

In another embodiment, the size of the shell fragments formed after microbubble collapse is adjusted by the inclusion of a shell component that have enhanced water solubility (or enhanced solubility relative to the surrounding liquid medium). In such a situation, and without being bound by any particular theory, during such microbubble collapse, the high solubility shell component is released from the shell and able to dissolve into the surrounding liquid medium, leaving residual shell components having lower solubility.

While glass microbubbles may be advantageous in certain settings due to their robust nature and resistance to bursting, methods and reagents must be employed when they are used to remove bound target cells since bursting is not an option. In addition, use of materials that do not degrade in the body such as glass must ensure complete removal of bead and bead materials prior to reinfusion to the patient. While this is possible in centralized manufacturing, it is a challenge in patient connected systems and significant methods and filtration and detection would need to be employed for such use. Such methods and reagents are described herein.

Figure 1:
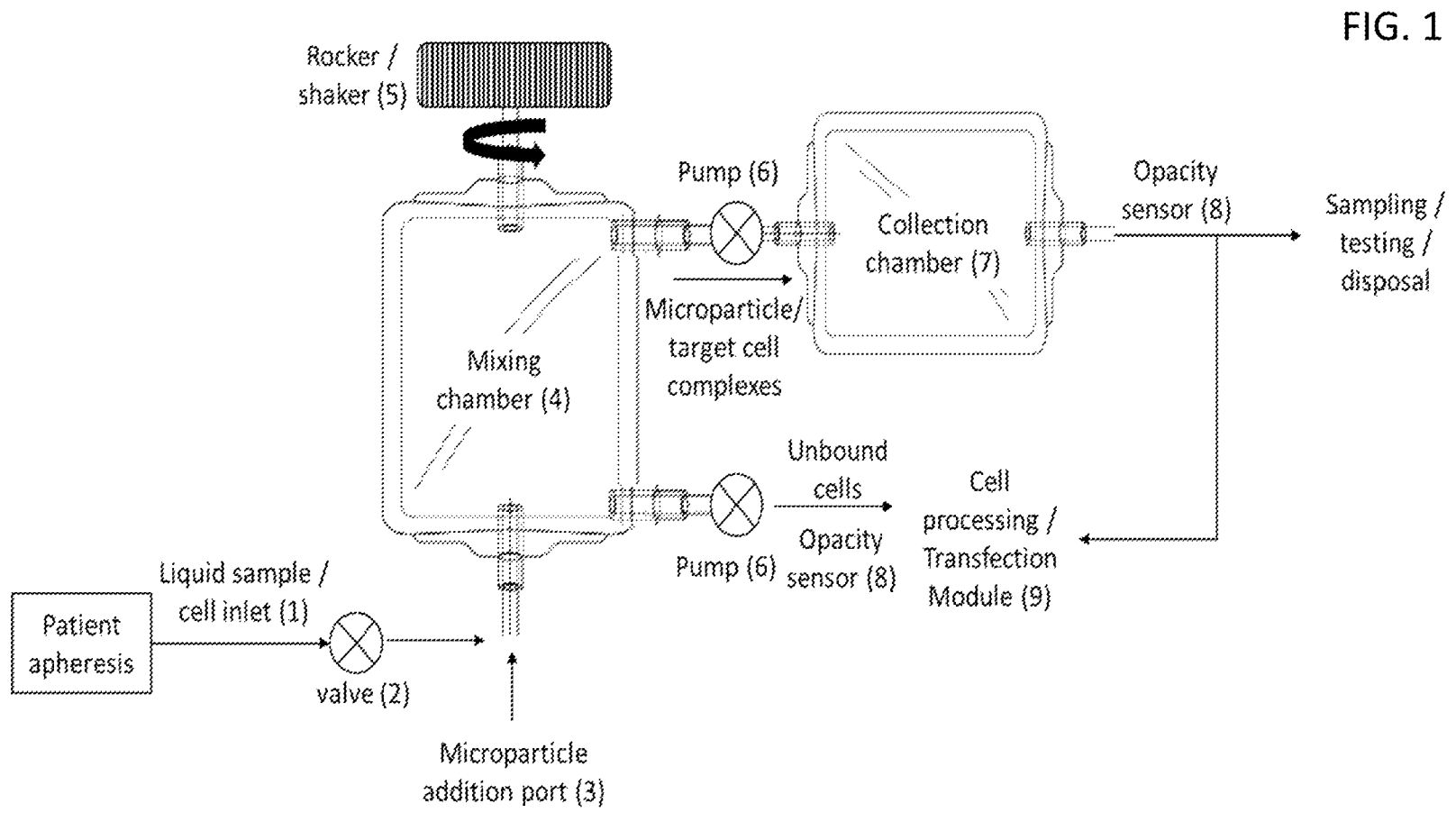

In certain embodiments an apparatus for use in the separation of components of a liquid sample by flotation having two interconnected chambers is provided [FIG. 1]. Liquid sample that is collected directly from a patient apheresis or leukopheresis machine/module is delivered in a closed loop via the liquid sample/cell inlet (1) into the first chamber, the mixing chamber (4), controlled by a flow valve (2). The mixing chamber (4) is composed of an outer housing that contains an inner chamber that can be a disposable bag, cylinder or compartment composed of, for example, polyvinyl chloride, polystyrene, polypropylene, polyolefin or another suitable material known in the art that can be replaced for each patient thereby ensuring no contamination between patients. This inner chamber directly contains any liquid sample material that enters from the cell inlet (1). The microbubble-containing sample is introduced through microparticle addition port (3) and drawn into the mixing chamber (4). Bound microbubble/target cell complexes are permitted or directed to enter the second chamber, the collection chamber (7) aided by a peristaltic or other pump (6). The collection chamber (7) is composed of an outer housing that contains an inner chamber that can be a disposable bag, cylinder or compartment composed of, for example, polyvinyl chloride, polystyrene, polypropylene, polyolefin or another suitable material known in the art that can be replaced for each patient thereby ensuring no contamination between patients. This inner chamber directly contains any liquid sample material that enters from the mixing chamber (4). Often, the chambers are provided in a manner such that the volume of fluid in each is variable and manipulatable. In an example of using such an apparatus, microbubbles and sample are introduced into the mixing chamber (4). A physical mixing process that is facilitated by a motorized rocker/shaker (5) connected to the mixing chamber (4) exerts continuous or periodic oscillation or agitation to permit microbubble/target cell mixing and complexation where the microbubbles bind target cells, if present and effervescent passage of microbubbles to the top of the mixing chamber (4). The bubbles, including microbubble/target cell complexes, are then permitted to float to the top surface of the fluid in the chamber. In cases where microbubbles are used to negatively select and bind target cells, the floating microbubble/target cell complexes at the top of the fluid surface are then transferred to the collection chamber (7) via positive displacement using a peristaltic or other pump thereby separating the microbubble/target cell complexes from the remainder of the fluid. The microbubbles can then burst, leaving the target cells. The inner disposable unit housed in the collection chamber (7) can optionally be detached from the apparatus in order for target cells to be further analyzed, processed or disposed of ex-vivo. The remaining cells near the bottom of the mixing chamber (4) are then transferred to a subsequent cell processing or transfection module (9) via positive displacement using a peristaltic or other pump. An opacity sensor (8) is used to measure the cell concentration of cells prior to proceeding to the cell processing or transfection module.

While the shapes, arrangements and orientations of the chambers, pumps, valves, rocker/shaker, sensors are depicted in a specific manner, this is intended to be exemplary only. A variety of adaptions to the depicted system are contemplated and discussed herein within the scope of the present disclosure.

In cases where microbubbles are used to positively select and bind target cells, microbubble/target cell complexes in the collection chamber (7) will be transferred to a subsequent cell processing/transfection module (9) via positive displacement using a peristaltic or other pump. An opacity sensor (8) is used to measure the cell concentration of cells prior to proceeding to the cell processing or transfection module (9). The apparatus contemplated in the present disclosure are provided for use in closed-loop continuous flow or batch processing. As such, a continuous feed of sample is provided and microbubbles can be continuously introduced to the sample feed. Separation similar to the dual chamber separation noted above and herein is provided often in a mixing chamber (4) in the continuous flow setting. The apparatus is in certain embodiments provided with one or more separation chambers permitting the introduction of microbubbles to the sample, and the sample flow is provided in a manner such that it flows through the one or more separation chambers one or more times to increase the yield of microbubble/target cell complexes.

One category of contemplated separation techniques utilizes magnetic particles as a support bound to or with a targeting moiety. Manipulation of magnetic particles includes the directed movement, focusing and/or trapping of magnetic particles.

One such technique utilizes magnetic, paramagnetic or superparamagnetic particles (e.g., MACS® MicroBeads or Dynabeads®). Superparamagnetic particles exhibit magnetic properties only in the presence of a magnetic field. Superparamagnetic polymer particles may be coated with a specific targeting moiety and added to a heterogeneous target suspension to bind a desired cell. Once bound, the resulting target cell/superparamagnetic particle complex may be pulled and magnetically-bound to a specific location in the volume of sample subject to separation, and unbound parts of the sample (e.g., target-free remaining sample) may then be moved away from the withdrawn from the target cell/superparamagnetic particle complex. Alternatively, a first antibody having specificity for the target cell may first be added to the sample containing target cells. Thereafter, unbound antibody is removed from the sample and magnetic particles carrying a second antibody having specificity—for the first antibody are introduced to the sample to bind the first antibody bound to the target cells. Magnetic separation is then performed.

The process of incubating cells with magnetic particles to provide for attachment of the magnetic particles with cells is generally defined by a predetermined time duration, for example, between at or about 5 minutes to at or about 15 minutes. In certain often included embodiments, the incubation and/or agitation time is less than at or about 15 minutes. In certain embodiments, the incubation and/or agitation time is greater than at or about 15 minutes. In certain embodiments, the incubation and/or agitation time is less than at or about 10 minutes. In certain embodiments, the incubation and/or agitation time is less than at or about 5 minutes. In certain embodiments, the incubation and/or agitation time is between at or about 5 minutes to at or about 10 minutes.

It must be observed that the present methods and systems are adapted to preserve the integrity and functioning of target cells. Therefore, magnetic particles (and indeed all particles, beads and microbubbles) should be used in a manner that achieves these objectives. With regard to magnetic particle separation care must be taken. Due to the speed at which magnetic particles travel though a sample when placed under a magnetic force, the particles can possibly damage target cells in the sample. Modulating the applied magnetic forces to effect separation may be employed here in addition to selecting optimal particle sizes and concentrations used in samples.

Although target cell separation efficiency is high, issues regarding removal of the magnetic (and other non-microbubble beads or particles contemplated herein) from target bound cells can add extra time and steps to the contemplated systems and methods. One exemplary separation technique involves the use of a polyclonal antibody that reacts with Fab-fragments of monoclonal antibodies comprising the targeting moiety to effect direct dissociation of the antigen-antibody binding. This technique is suitable for use with certain types of polymer particle and certain monoclonal antibodies. Other known methods involve incubation at 37° C., enzymatic cleavage, and/or the introduction of reagents that compete for the same target as the polymer particles.

Methods for preparing magnetic particles for the present systems and methods can employ a variety of methods known in the art, such as dispersing magnetic particles within a polymeric matrix during preparation, constructing a magnetic material shell around a polymeric particle core, or introducing magnetic material into preexisting pores within the polymer particles. Another known method involves creating bare magnetic material particles first that serve as the core and constructing a shell/coating around the magnetic material core. Silane or silane-based coatings are known such coating materials, in addition to coatings including polyglutaraldehyde, acrylamide, n-butylacrylate, or N,N'-methylenebisacrylamide, polyvinyl alcohol, natural polymers such as dextran, and/or bovine serum albumin. In the presently contemplated embodiments, these magnetic particle coatings serve as substrates to which additional biomolecules such as targeting moieties are conjugated or otherwise introduced or attached.

In certain embodiments, the shell is a silane layer formed from organofunctional alkoxysilane molecules, optionally organofunctional alkoxysilane molecules that comprise a couplable end group, optionally a couplable end group selected from the group consisting of an amino, sulphydryl, carboxyl, and hydroxyl end or reactive group. The end group may be protected or unprotected. If protected, a deprotection step is preferably used prior to coupling of the protein/polymer composite layer. In certain embodiments, the protein/polymer composite layer is covalently bound to the glass shell. Often in such embodiments, the protein/polymer composite layer is comprised of serum albumin, e.g., bovine or human serum albumin, dextran, or casein. In other embodiments, the protein/polymer composite layer is permanently bound by heating the composition from about 45° C. to about 85° C. The targeting moiety or bioaffinity ligand (i.e., one member of a high affinity binding pair) is then conjugated, preferably covalently, to the protein/polymer layer.

Frequent targeting moieties include, as discussed herein, antibodies, antigen-binding antibody fragments, cell surface receptors, ligand-binding extracellular domains of cell surface receptors, nucleic acids (including nucleic acid-based aptamers), avidin, streptavidin, and/or biotin.

The targeted nanomagnetic particles of the invention often behave as stable colloids when combined in a sample such as whole blood or a fraction of whole blood. Moreover, targeted nanomagnetic particles of the invention often exhibit no significant or deleterious change in magnetic, bioaffinity, and/or particle size and targeting properties during storage over prolonged periods.

Nanomagnetic particles often have diameters tailored to the application for target cell (e.g., nucleated blood cell) separation, ranging from about 5 nm to about 500 nm can be utilized according to the present disclosure, often from about 30 nm to about 300 nm. Also often, nanoparticles of the present disclosure include a magnetic core particle comprised of a ferrous oxide, chromium oxide, or another stable metal oxide that comprises a substituted metal ion such as, for example, Mn, Co, Ni, Zn, Gd, and/or Dy.

Magnetic forces contemplated herein refer to the forces acting on the particle due to the application of a magnetic field. Whether there is a magnetic force acting on a particle depends on the difference in the volume susceptibility between the particle and its surrounding medium. The particle velocity under the balance between magnetic force and viscous drag can be calculated and adjusted to achieve a desired or predetermined level of magnetic force and therefore manipulation force. Such magnetic manipulation force will often account for the volume susceptibility of the magnetic particles; magnetic field strength, magnetic field strength gradient, density of the surrounding sample medium, and/or viscosity of the surrounding sample medium. Magnetic fields are established in sample chambers by applying electric currents to, for example, microelectromagnetic elements or by placing a permanent magnet in close proximity of a chamber or column. Each microelectromagnetic element is capable of producing magnetic field upon applying DC and/or AC electric currents. An electromagnetic element may be an electric wire wrapped as a loop, or an electric coil wrapped around a magnetic core. Alternatively, an electromagnetic chip may be included that has an array of individually addressable electromagnetic units. These units are positioned or structurally arranged in certain order so that when each of or some of or all of electromagnetic units are energized (=magnetized), desired magnetic field distributions can be established to produce magnetic forces acting on magnetic particles in the sample. In related embodiment, the electromagnetic chip may include multiple, interconnected electromagnetic units and these units are turned on or off in a synchronized order. Yet, in another related embodiment, the electromagnetic chip includes one or more electromagnetic unit that can be energized to produce a magnetic field. Such electromagnetic elements are often incorporated in the systems of the present disclosure when magnetic particle separation is utilized.

The apparatus contemplated in the present disclosure, such as that depicted in FIG. 2, are provided for use in closed-loop continuous flow. As such, a continuous feed of sample is provided and magnetic nanoparticles may be continuously introduced to the sample feed through the microparticle and reagent addition port (10). Liquid sample that is collected directly from an apheresis or leukopheresis machine and delivered in a closed loop via the liquid sample/cell inlet (1) and into the separation chamber (11) controlled by a flow valve. The separation chamber (11) is composed of an outer housing that contains an inner chamber, separation chamber disposable unit (13), that can be a disposable bag, cylinder or compartment composed of, for example, polyvinyl chloride, polyolefin or another suitable material known in the art that can be replaced for each patient thereby ensuring no contamination between patients. This inner chamber directly contains any liquid sample material that enters from the cell inlet (1). Alternatively or in addition the fluid sample, or a portion of the sample may be provided to flow in a continuous loop though the separation chamber (11) such that the cells in the sample or portion thereof cycle through the separation chamber (11) two or more times, each time being subject to physical interaction with the magnetic nanoparticles.

Figure 3:
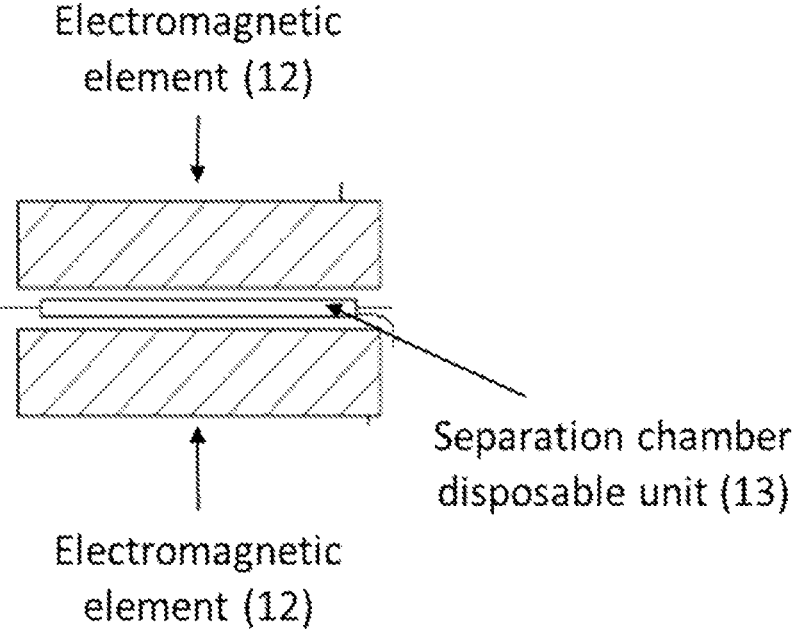
FIG. 3 depicts a different view of the separation chamber relative to electromagnetic elements of the schematic for a continuous magnetic nanoparticle module of the presently described systems.

In certain embodiments such as the embodiment of FIG. 3, the separation chamber is adapted to apply the electromagnetic force generated by electromagnetic elements (12) placed on both sides of the separation chamber disposable unit (13) transverse to the flow of the fluid sample in/through the separation chamber disposable unit (13) permitting magnetic nanoparticle/target cell mixing and complexation where the magnetic nanoparticle binds target cells in the presence of the electromagnetic elements (12).

The magnetic nanoparticle/target cell complexes remain bound and stationary along the side walls of the separation chamber (11), permitting remaining unbound and noncomplexed cells in the liquid sample to continue to flow and be transferred to a subsequent cell processing or transfection module (9) via positive displacement using a peristaltic or other pump (14). An opacity sensor (8) is used to measure the cell concentration of cells prior to proceeding to the cell processing or transfection module. A valve (15) can be engaged at any point after remaining unbound cells in the liquid sample are transferred to the cell processing or transfection module to confine the magnetic nanoparticle/target cell complexes inside the separation chamber (11). The separation chamber (11) can be optionally detached from the apparatus in order for target cells to be further analyzed, processed or disposed of. While the shapes, arrangements and orientations of the chambers, pumps, valves, ports, sensors and electromagnetic elements are depicted in a specific manner, this is intended to be exemplary only. A variety of adaptions to the depicted system are contemplated and discussed herein within the scope of the present disclosure.

In some embodiments, a cell separation module comprises an enrichment unit that uses magnetic beads coated with antibodies as the targeting moiety against one or more specific cell-surface antigens to perform one or more selection steps on the cells following cell separation of whole blood or body fluid. This causes the cells expressing this antigen to attach to the magnetic beads. When exposed to a strong magnetic field, such as a magnet, the cells attached to the beads (expressing the cell-surface marker) are pulled to a specific location, while or before cells not expressing the cell-surface marker are physically separated from the cells expressing the cell-surface marker. Using this method, cells can be selected positively or negatively, or using a combination of positive and negative selection, with respect to the particular cell-surface markers.

These or other beads or particles may be utilized by the presently described systems and in methods of their use. As observed above, the inventors have provided certain limitations regarding the suitability of beads in the contemplated patient-connected systems. For example, DYNAL beads or other beads that are reactive, large, present difficulty in separation from target cells, or have other properties that are either harmful to the patient or the processing of the closed-loop system, slow the process of moving to a cell transduction step or module, or slow or adversely affect a cell transduction process are excluded from the contemplated beads of the present disclosure. Further, it is contemplated that a highly selective filtration or particle separation system is utilized to purify any cell of any cell population that has had contact with a bead or particle of the present disclosure and is destined to return to the patient in the present patient-connected systems prior to re-introducing the cell to the patient. The filtration or particle separation system, when included, is part of the patient-connected, closed-loop system.

One exemplary method and system utilizes low density polypropylene beads coated with a monoclonal antibody. The target cells bind to the monoclonal antibodies attached to the low density polyethylene or polypropylene beads and float or are otherwise manipulated, to the surface of the suspension where they may be removed by, for example, decantation.

Beads or particles useful in the methods and systems of the present disclosure may include hollow particles having an at least partially solid outer region or shell and a hollow or different density inner region or core. The beads or particles may be buoyant particles and can include plastic beads (e.g., polypropylene beads, polyethylene beads, etc.), glass beads, lipid beads (e.g., stabilized liposome-based beads), hollow beads, solid beads, liquid-filled beads, gas-filled beads, and any other suitable type of particle, and/or combinations thereof.

For example, in certain embodiments, such beads or particles may have a substantially spherical hollow inner region encased by an outer region having a hardness higher than that of microbubbles discussed herein. In certain embodiments, the core of the beads or particles may be void of fluid, or be filled with a gas, including, but not limited to oxygen, nitrogen, carbon dioxide, helium, fluorocarbon gases and various combinations thereof, such as air. The shell may be any material that can encase a volume of fluid, for example, a solid such as a metal, glass, ceramic, or similar material. For example, the outer region may include a siliceous material having a siliceous surface. In one embodiment, the hollow particles may include glass bubbles, such as those sold by 3M under the trade designation SCOTCHLITE® glass bubbles.

Generally, the beads or particles of the present disclosure are produced, adapted and/or sized to facilitate rapid separation from a solution based, for example, on buoyancy forces. Moreover, such particles are sized to optimize target cell capture and avoid target cell damage during use in separation. The particles may have an average density of, for example, less than about 1 g/ml, less than about 0.8 g/ml, less than about 0.6 g/ml, or even less than about 0.4 g/ml. In some embodiments, the particles may have an average density in a range of from about 0.05 g/ml to about 0.8 g/ml. The particles may have a mean particle size of less than about 200 μm, less than about 100 μm, or even less than about 80 μm. In illustrative embodiments, the particles may have a mean particle size in a range of from about 5 to 250 μm, from about 10 to 100 μm, or from about 20 to 80 μm.

The beads or particles may be surface modified involving, for example, multiple steps. Cleaning and alkaline, acid, and/or plasma treatment may be included initially to prepare the surface. Thereafter, the beads or particles are introduced to a treatment solution that includes one or more surface-modifying agents and one or more solvents, thereby producing particles having the surface-modifying agents bonded to or otherwise exhibited on the exterior surface of the particles. In various embodiments, the surface-modification treatment solution may include one or more solvents (e.g., organic and inorganic liquids (including water) or plasticizers known to be used or useful to dissolve or soften other organic or inorganic materials) and one or more surface-modifying agents. The ratio of surface-modification treatment solution to particles can be tuned, for example, to control the amount of modifying agent that is coupled to the particles. In some embodiments, following surface modification of the particles in a treatment solution, the surface-modified particles are separated from the treatment solution, optionally washed, and dried.

The present disclosure involves separating target cells from solution or isolating target cells in solution. Beads or particles contemplated herein may be utilized in related processes and systems. To do so, surface-modified beads or particles are contacted with a solution having one or more analytes capable of coupling to the surface-modifying agent on the bead or particle, thereby generating surface-modified beads or particles carrying an analyte. The present disclosure also often further includes mixing/agitation to achieve dispersion of the surface-modified particles throughout the solution. The process of incubating cells with particles and mixing/agitating the combined cells with particles to provide for attachment of the particles with cells is generally defined by a predetermined time duration, for example, between at or about 5 minutes to at or about 30 minutes. In certain often included embodiments, the incubation and/or agitation time is less than at or about 30 minutes. In certain embodiments, the incubation and/or agitation time is greater than at or about 5 minutes. In certain embodiments, the incubation and/or agitation time is less than at or about 20 minutes. In certain embodiments, the incubation and/or agitation time is less than at or about 10 minutes. In certain embodiments, the incubation and/or agitation time is between at or about 10 minutes to at or about 20 minutes.

The surface-modified hollow beads or particles of the present disclosure facilitate rapid separation of the target cells from samples. For example, in embodiments in which the particles are separated by flotation to an upper surface of the solution, the particles of the present disclosure separate in between about 5 to 15 minutes. In certain often included embodiments, the particles of the present disclosure separate in less than at or about 5 minutes, less than at or about 4 minutes, less than at or about 3 minutes, less than at or about 2 minutes, less than at or about 1 minute, less than at or about 30 seconds, or less than at or about 15 seconds. Additional processes such as centrifugation may be employed to decrease separation times.

The processed bead or particle can include any number of surface modifications arranged (e.g., layered) in any suitable way. In some variations, additional or alternative to those described above, the processed bead or particle includes any or all of: proteins to modulate the texture or physical properties of the shell to improve a binding ability of the shell; a shell such as a polymer shell that functions, for instance, to prevent leeching of one or more components of the buoyant particle into the surrounding solution; and a change in charge (e.g., applied charge, induced charge, switched charge, etc.) of the buoyant particle surface which can function, for instance, to enable DNA capture (e.g., based on charge switching of silica).

In certain embodiments, the beads or particles includes silica beads having a density less than that of fluid of the sample. These silica beads are treated with a moiety (e.g., Streptavidin for biotin binding, an antibody for formation of an antibody-antigen complex, another moiety, etc.) configured to selectively couple with a targeting moiety or the target cell. In other embodiments, the beads or particles include borosilicate glass that can include a particle shell surrounding a particle core. As noted, the particle shell of the glass microparticles can be coated with, for example, an aminosilane layer to allow for subsequent surface functionalization with targeting moieties. After functionalization, the glass microparticles can be crosslinked to streptavidin or another suitable surface functionalization chemical procedure such as pegylation, click chemistry, layer-by-layer assembly, ink-jet printing, etc. for selective capture of target cells.

As noted, the beads or particles can also be configured with moieties for binding to the target cell and can include any one or more targeting moieties such as: charge-based moieties, nucleic acid-targeting moieties, protein-based moieties (e.g., cell adhesion molecules, growth factors, synthetic proteins), or another suitable moiety. aggregating the population of target-bound complexes at a collection region of the process chamber, which functions to aggregate the population of target-bound complexes to at least one desired region of the process chamber, in order to facilitate extraction of the target constituent from the sample in an efficient manner. Interactions (e.g., hydrophobic interactions, hydrophilic interactions, neutral interactions) between fluid of the sample and the process chamber, and/or the method of separation (e.g., passive buoyant separation, active buoyant separation, compound density gradient, etc.) can affect the location(s) of the collection region(s) of the process chamber at which the population of target-bound complexes reside.

In certain embodiments an apparatus for use in the separation of components of a liquid sample by flotation having two interconnected chambers is provided. The two chambers are situated such that a buoyant bead/particle-containing sample is drawn into one chamber and bound buoyant bead or particle/target cell complexes are permitted or directed to enter the second or another chamber. Often, the chambers are provided in a manner such that the volume of fluid in each is variable and manipulatable. In an example of using such an apparatus, buoyant bead/particle and sample are introduced into the first chamber. A physical mixing process, centrifugation process, or an effervescent passage of buoyant bead/particle is permitted to occur, where the buoyant bead/particle bind target cells, if present. The buoyant bead/particle, including buoyant bead or particle/target cell complexes, are then permitted to float to the top surface of the fluid in the chamber. The floating bead or particle/target cell complexes at the top of the fluid surface (or another predetermined location in a chamber) are then transferred to the second chamber by a physical fluid transfer process, thereby separating the bead or particle/target cell complexes from the remainder of the fluid. The bead or particles are then separated from the target cells with methods and/or reagents contemplated herein.

The apparatus contemplated in the present disclosure are provided for use in closed-loop continuous flow. As such, a continuous feed of sample is provided and buoyant beads/particles are continuously introduced to the sample feed. Separate similar to the dual chamber separation noted above and herein is provided often in a single chamber in the continuous flow setting. The apparatus is in certain embodiments provided with one or more separation chambers permitting the introduction of buoyant beads/particles to the sample, and the sample flow is provided in a manner such that it flows through the one or more separation chambers one or more times to increase the yield of bead or particle/target cell complexes.

Two-step purification is also employed in certain embodiments, including embodiments of each of the systems contemplated herein utilizing particles, including microbubbles and magnetic particles among other embodiments. In such two-step purification the patient sample is subjected to a negative clearance or separation to remove cells not of interest in the desired therapeutic intervention such as, for example, red blood cells, platelets, polymorphonuclear leukocytes. After this step, the sample remaining after this negative clearance or separation is subjected to a purification and enrichment of target cells using particles and the methods and systems contemplated herein.

Biological cells have different dielectric properties, as defined by their permittivity and conductivity, and experience different dielectrophoretic forces.

For traveling-wave dielectrophoretic manipulation of target cells, traveling-wave dielectrophoretic forces acting on a cell 10 µm diameter can vary somewhere between 0.01 and 10000 pN.

A traveling wave electric field can be established by applying appropriate AC signals to microelectrodes appropriately arranged on an exemplary system. For generating a traveling-wave-electric field, application of a plurality of electrical signals, each having a different phase value, is often required. One such example involves producing a traveling wave electric field is to use four phase-quadrature signals (0, 90, 180 and 270 degrees) to energize four linear, parallel electrodes patterned on the applicable sample-containing system surfaces. These electrodes are adapted to form a repeating unit. Moreover, two or more two such units may be adjacently located to produce a traveling-electric field in the spaces near the electrodes. Though not intending to be bound by any specific theory, as long as electrode elements are arranged following certain spatially sequential orders, applying phase-sequenced signals will result in establishing traveling electrical fields in the region near to the electrodes.

Both dielectrophoresis and traveling-wave dielectrophoresis forces acting on target cells depend on not only the field distributions (e.g., the magnitude, frequency and phase distribution of electrical field components; the modulation of the field for magnitude and/or frequency) but also the dielectric properties of the target cells and the sample medium. For dielectrophoresis, if target cells are more polarizable than the medium (e.g., having larger conductivities and/or permittivities depending on the applied frequency), target cells will experience positive dielectrophoresis forces and are directed towards the strong field regions.

The target cells that are less polarizable than the surrounding medium will experience negative dielectrophoresis forces and are directed towards the weak field regions. For traveling wave dielectrophoresis, target cells may experience dielectrophoresis forces that drive them in the same direction as the field traveling direction or against it, depending on the polarization factor.

Another method of cell separation involves acoustic force application. Acoustic force refers to the force that is generated on target cells or target cell complexes with beads, particles, or microbubbles (target cell associated complexes) contemplated herein, by an acoustic wave field. The acoustic forces are used to for manipulate, e.g., trap, move, direct, handle, mix, target cells in the sample. The use of the acoustic force in a standing ultrasound wave for target cell manipulation has been demonstrated for concentrating, aggregating and/or sedimenting cells Electrostatic and acoustic radiation forces may also be combined to separate target cells or associated complexes. It has been shown that acoustic radiation force causes little or no damage in the manipulation of mammalian cells in terms of ion leakage or antibody production.

An acoustic wave can be established by an acoustic transducer, e.g., piezoelectric ceramics such as piezoelectric material. When AC voltages are applied to a piezoelectric transducer, a vibration occurs that is transmitted into a sample surrounding the piezoelectric transducer.

Ultrasonic transducers generate a three-dimensional or multi-dimensional acoustic standing wave in the fluid that exerts a lateral force on the trap target cells or associated complexes to accompany the axial force so as to increase the trapping and clumping capabilities of the standing wave. The contemplated lateral force is about even with the axial force, though other adaptations are contemplated. Perturbation of the piezoelectric element in an ultrasonic transducer in a multimode fashion allows for generation of a multidimensional acoustic standing wave. A piezoelectric element can be specifically designed to deform in a multimode fashion at designed frequencies, allowing for generation of a multi-dimensional acoustic standing wave. The multi-dimensional acoustic standing wave may be generated by distinct modes of the piezoelectric element such as the 3×3 mode that would generate multidimensional acoustic standing waves. A multitude of multidimensional acoustic standing waves may also be generated by allowing the piezoelectric element to vibrate through many different mode shapes. Thus, the piezoelectric element would excite multiple modes such as a 0×0 mode (i.e. a piston mode) to a 1×1, 2×2, 1×3, 3×1, 3×3, and other higher order modes and then cycle back through the lower modes of the piezoelectric element (not necessarily in straight order), or the excitation may be a weighted combination of several modes. This switching of the piezoelectric element between modes allows for various multidimensional wave shapes, along with a single piston mode shape to be generated over a designated time.

The contemplated acoustophoretic separation technology employs, for example, ultrasonic acoustic standing waves to trap target cells or associated complexes in a volume of sample. The target cells or associated complexes collect at the nodes or anti-nodes of the acoustic standing wave, depending on the target cells or associated complexes acoustic contrast factor relative to the sample, forming clusters/clumps/agglomerates/coalesced droplets that continuously fall out of the acoustic standing wave when the clusters have grown to a size large enough to overcome the holding force of the acoustic standing wave (e.g. by coalescence or agglomeration) and the target cell or associated complex density is higher than the host fluid, or to rise out of the acoustic standing wave when the target cell or associated complex fluid density is less than the host fluid. Such acoustic radiation force is proportional to the target cell or associated complex volume (e.g. the cube of the radius) when the target cell or associated complex is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the target cell or associated complex to the stable axial positions within the standing waves. When the acoustic radiation force exerted on the target cell or associated complex is stronger than the combined effect of fluid drag force and buoyancy and gravitational force, the target cell or associated complex is trapped within the acoustic standing wave field. This results in concentration, agglomeration and/or coalescence of the target cells or associated complexes. The strong lateral forces create rapid clustering of target cells or associated complexes. In the case of a sample having several different target cell or associated complex sizes, it is possible by tuning of the system parameters to settle out the group of target cells or associated complexes that are larger in size whereas the group of target cells or associated complexes smaller in size can be kept in suspension. These two layers are then harvested separately. A repeated process can then be used to fractionate groups of different sized target cells or associated complexes according to size.

The acoustic contrast factor is a function of the ratio of target cell or associated complex to fluid compressibility and target cell or associated complex to fluid density. Most cell types present a higher density and lower compressibility than the medium in which they are suspended, so the acoustic contrast factor between the target cell or associated complex and the sample medium has a positive value. As a result, the axial acoustic radiation force drives the target cell or associated complex, with a positive contrast factor, to the pressure nodal planes, whereas other cells or particles with a negative contrast factor are driven to the pressure anti-nodal planes (or vice versa). The radial or lateral component of the acoustic radiation force is larger than the combined effect of fluid drag force and gravitational force. The radial or lateral component drives the target cells or associated complexes to specific locations (points) within these planes where they cluster, clump, agglomerate, or coalesce into larger groups, which will then continuously gravity separate from the fluid.

Through the use of acoustophoresis, the separation of the target cells can be continuous and efficient. As desired, the acoustophoresis process may also be coupled with a filtration process upstream or downstream, such as depth filtration, tangential flow filtration (TFF), or other physical filtration processes.

The apparatus contemplated in the present disclosure are provided for use in closed-loop continuous flow. As such, a continuous feed of sample is provided and subjected to a standing surface acoustic wave or travelling surface acoustic wave, for example, oriented at an optimum angle to the flow of the sample. One specifically contemplated set of embodiments in this regard include the use of a tilted-angle standing surface acoustic wave. A piezoelectric wave generator/transducer may be employed to crate the acoustic wave. An acoustofluidic waveguide may be employed to direct the contemplated acoustic wave. Separation chamber adaptations to provide for acoustic separation are known in the art.

This module may be utilized in a stand-alone or a two-step purification process and in this regard will often serve as at least a component of the negative clearance or separation to remove platelets or another blood component from target cells. Alternatively, the acoustic wave may be adapted to separate a target cell bound particle from non-target cells or other blood components in a cell purification/enrichment step or module of the present systems.

In some embodiments, the cell purification module comprises a cell separator such as an apheresis device. Non-limiting examples of currently used apheresis devices include, for example: COBE® Spectra, TRIMA®, and SPECTRA OPTIA® systems (all marketed by Gambro BCT) and the AMICUS™ and CS-3000+™ (marketed by Fenwal/Baxter) devices. Systems or devices used for cell enrichment and purification purposes include, for example, the BAXTER ISOLEX 300I™ and the Miltenyi CLINI-MACS™, which enrich PBPC (peripheral blood progenitor cells) based on a specific ligand (CD34, both devices and CD133 Miltenyi) on the cells' surface. Other stand-alone devices, such as the Gambro COBE 2991™ Blood Cell Processor or the Fresenius Kabi Lovo™ or Baxter CYTO-MATE™ Cell Washing System are often used to wash, concentrate, or place cells into appropriate growth or infusion medium.

In some embodiments, the cell purification module can comprise a centrifuge for processing blood cells and separating blood into its component parts using centrifugal forces.

A cell purification module of this design, and others described herein, can comprise a user interface with integrated monitor and/or computer processor for storing and performing different cell processing operations.

Filters, filtering systems, methods, and devices, particularly those adapted for apheresis of cellular bodies, can also be components of a cell purification module as described herein. A "filter" is a structure that comprises one or more pores or slots of particular dimensions (that can be within a particular range), that allow the passage of some sample components but not others from one side of the filter to the other, based on the size, shape, and/or deformability of the components. A filter can be made of any suitable material, such as metal, ceramics, glass, silicon, plastics, polymers, fibers (such as paper or fabric), etc. that prevents passage of insoluble components. A "filtration unit" is a filtration chamber and the associated inlets, valves, and conduits that allow sample and solutions to be introduced into the filtration chamber and sample components to be removed from the filtration chamber. A filtration unit optionally also comprises a loading reservoir, in some embodiments.

In some embodiments, a filtration chamber used in the cell purification module is a chamber that comprises or engages at least one microfabricated filter enclosed in a housing. The surface of the filter and/or the inner surface of the housing can be modified by vapor deposition, sublimation, vapor-phase surface reaction, or particle sputtering to produce a uniform coating, in some embodiments. A filtration chamber can comprise one or more fluid-impermeable materials, such as but not limited to, metals, polymers, plastics, ceramics, glass, silicon, or silicon dioxide. Preferably, a filtration chamber has a volumetric capacity of from about 0.01 milliliters to about ten liters, more preferably from about 0.2 milliliters to about two liters. In some embodiments of the systems described herein, a filtration chamber can have a volume of from about 1 milliliter to about 80 milliliters.

A filtration chamber used in the systems described herein can comprise or engage any number of filters. Various filter chamber configurations are possible. A filter can be provided as a wall of a chamber, or internal to a chamber, and filters can optionally be provided in tandem for sequential filtering. Where filters are inserted into a chamber, they are inserted to form a tight seal with the walls of a chamber, such that during the filtration operation, fluid flow through the chamber (from one side of a filter to the other) must be through the pores of the filter. A filtration chamber can also optionally have one or more additional ports for the additions of one or more reagents, solutions, or buffers.

In some embodiments, filtration chambers for use with the systems and methods described herein allow for the passage of mature red blood cells (lacking nuclei) through the channels and thus out of the chamber, while not or minimally allowing cells having a greater diameter or shape (for example but not limited to, nucleated cells such as white blood cells and nucleated red blood cells) to exit the chamber. For example, a filtration chamber having a slot width between 2.0 and 4.0 microns would allow the double-discoid-shaped RBCs to go through the slots while primarily retaining the nucleated RBCs and WBCs with diameters or shapes larger than 7 microns.

Filters can include treatment or modifications to the surface of a filter and/or the inner surface of a housing that encloses the filter to improve its filtering efficiency. In some embodiments, the surface treatment produces a uniform coating of the filter and the housing. In some embodiments, one or both surfaces of the filter is treated or coated or modified to increase its filtering efficiency. In some embodiments, one or both surfaces of the filter is treated or modified to reduce the possibility of sample components (such as but not limited to cells) interacting with or adhering to the filter.

A filter and/or filter chamber can be physically or chemically treated, for example, to alter surface properties (e.g., hydrophobic, hydrophilic), and thereby reduce the interaction of sample components with the filter and/or housing surface, in some embodiments. For example, vapor deposition, sublimation, vapor-phase surface reaction, or particle sputtering are some of the methods that can be used to treat or modify the surface of a filter and/or filter chamber. Any suitable vapor deposition methods can be used, e.g., physical vapor deposition, plasma-enhanced chemical vapor deposition, chemical vapor deposition, etc. Suitable materials for physical vapor deposition, chemical vapor deposition, plasma-enhanced chemical vapor deposition or particle sputtering may include, but are not limited to, a metal nitride or a metal halide, such as titanium nitride, silicon nitride, zinc nitride, indium nitride, boron nitride, Parylene or a derivative thereof, such as Parylene, Parylene-N, Parylene-D, Parylene AF-4, Parylene SF, and Parylene HT, Polytetrafluoroethylene (PTFE) or Teflon-AF can also be used for chemical vapor deposition.

In some embodiments, traveling-wave dielectrophoretic forces can be generated by electrodes built onto a chip that is part of a filtration chamber, and can be used to move sample components such as cells away from a filter. In this case, the microelectrodes are fabricated onto the filter surfaces and the electrodes are arranged so that the traveling wave dielectrophoresis can cause the sample components such as cells to move on the electrode plane or the filter surface through which the filtration process occur.

A filtration chamber can also comprise a component that comprises electromagnetic elements. Such electromagnetic elements can be used for the capture of a target cell or other sample component before, during or after filtering of the sample. Target cells components can be captured after being bound to magnetic beads, as described above.

An acoustic force chip, e.g., as described above, can also engage or be part of a filtration chamber, or one or more acoustic elements can be provided on one or more walls of a filtration chamber, in some embodiments. Mixing of a sample by the activation of the acoustic force chip can occur during the filtration procedure. Preferably, a power supply is used to transmit an electric signal to the acoustic elements of one or more acoustic chips or one or more acoustic elements on one or more walls or a chamber. One or more acoustic elements can be active continuously throughout the filtration procedure or can be activated for intervals (pulses) during the filtration procedure.

In some embodiments of the modules described herein, a cylindrical filter that employs a thin micro-machined porous filter membrane with a regular array of pores that can reliably pass blood while trapping cells from the blood can be used.

The cell purification module collects bulk cells from the patient blood or other body fluid received through the inlet conduit and allows for the separation and collection of certain cells from the fluid.

In addition, the cell purification module enriches for one or more target cell (including predetermined cells and populations thereof, e.g., nucleated blood cells) from the bulk fluid such as a fluid sample. Accordingly, techniques and methods are integrated to further separate cell populations or to select for a particular target cell type or class, e.g., all lymphocytes, or all T cells, among others. Such techniques include but are not limited to methods and systems described herein, including buoyancy-based separation (microbubbles and buoyant beads and particles), magnetic separation, filtration, immunoaffinity separation, gravitation separation, density gradient separation, elutriation, acoustic separation, electrophoretic separation, and any combinations thereof. The cell separation module can employ any of these or other methods known in the art for further enriching for and/or obtaining a target population of cells from a patient.

Target cell populations refer to cells that are enriched from blood or other body fluid. The terms "enriching" or "enriched" are used interchangeably herein and mean that the yield (fraction) of cells of one type, such as, for example, T cells, for use in the systems and methods described herein, is enriched to at least at or about 50%, at least at or about 55%, at least at or about 60%, at least at or about 65%, at least at or about 70%, at least at or about 75%, at least at or about 80%, at least at or about 85%, at least at or about 90%, at least at or about 95% over the fraction of cells of that type in the starting sample. The enrichment of the target cell population can be adapted to enrich to a percentage purity and/or eliminate a particular target cell or cell types from the population.

Non-limiting examples of cell types that can be enriched from a leukapheresis bulk product include B lymphocytes, T lymphocytes, CD4 and CD8 T lymphocytes, dendritic cells, monocytes, macrophages, natural killer (NK) cells, NKT cells, T-regulatory cells, CD4 T-helper cells, CD8 cytotoxic T lymphocytes (CTLs), neutrophils, basophils, eosinophils, megakaryocytes, hematopoietic stem cells (HSCs), hematopoietic progenitor cells (HPCs), mast cells, subsets of such cells, and combinations thereof.

In some embodiments of the systems and methods described herein, enrichment of the target cell populations can be by chemical or physical means, e.g., capture, and the individual cells of the target cell populations are said to be isolated from the bulk blood cell population. The enrichment procedure in an enrichment module incorporated, e.g., within or as part of the cell purification module, can employ one or more methods known in the art including, without limitation, antigen capture, e.g., on filters, microbubbles, microbeads, nanomagnetic particles, other nanoparticles, fluorescence-activated cell sorting, microfluidics, solid support affinity, acoustics, bioluminescence, antibody tagging, or enzyme substrate.

Markers or determinants specific for target cell populations, e.g., T cell populations, can be used to isolate or enrich for these cells. A "marker," as used herein, refers to a known and identifiable characteristic and/or phenotype of a cell. Markers can be used for selection of cells comprising characteristics of interest. Markers vary based on the contemplated cell population. Markers can be, for example, molecules expressed by or on a given cell type, morphological, functional or biochemical (enzymatic). Preferably, such markers are proteins, and more preferably, proteins that possess an epitope for antibodies or other binding molecules available in the art. Examples of morphological characteristics or traits include, but are not limited to, shape, size, appearance (e.g., smooth, translucent), density, granularity, and nuclear to cytoplasmic ratio. Examples of functional characteristics or traits include, but are not limited to, the ability to adhere to particular substrates, certain motility characteristics, the ability to incorporate or exclude particular dyes, ability to migrate under particular conditions, and the ability to differentiate along particular lineages. Markers can be detected by any method available to one of skill in the art.

A cell separation module can include an enrichment unit that uses or exploits one or more "cell-surface determinants" or "cell-surface markers" for enrichment of a target cell population(s) using the separation or purification methods and systems contemplated herein (e.g., microbubbles, particles, beads, etc.). A "cell-surface marker" refers to any molecule that is expressed on the surface of a cell. Many naturally occurring cell-surface markers are termed "CD" or "cluster of differentiation" molecules. Cell-surface markers often provide antigenic determinants to which antibodies can bind. Non-limiting examples of human cell-surface markers useful for the systems and methods described herein are provided in Table 1.

TABLE 1

| B Cells | CD19, CD20 |
|---|---|
| T Cells | CD3, CD56(–), CD4, CD8 |
| Activated T cells | CD25, CD69 |
| Regulatory T Cells | CD25, CD127(–) |
| Gamma delta T cells | ☐☐chain☐☐☐chain |
| NK T cells | CD16, CD56, CD3 |
| Dendritic Cells | CD1c, CD83, CD141, CD209, MHC II, CD11c |
| Plasmacytoid Dendritic Cells | CD123, CD303, CD304 |
| Platelets (resting) | CD42b, CD41, CD61 |
| Platelets (activated) | CD62P |
| Natural Killer Cells | CD3(–), CD16, CD56 |
| Hematopoietic Stem or Progenitor Cells | CD34, CD90, CD135 |
| Macrophage | CD11b, CD68, CD163, CD33 |
| Monocyte | CD14, CD16, CD64 |
| Plasma Cells | CD138 |
| Red Blood Cells | CD235a |
| Neutrophils | CD15, CD16, CD49d(–) |
| Basophils | 2D7 antigen, CD117(–), CD123, CD203c, FcεRIα |
| Eosinophils | CD11b, CD193, EMR1, Siglec-8 |

A cell can be designated "positive" or "negative" for any cell-surface marker, and both such designations are useful in the systems and methods described herein. A cell is considered "positive" for a cell-surface marker if it expresses the marker on its cell-surface in amounts sufficient to be detected using methods known to those of skill in the art, such as contacting a cell with an antibody that binds specifically to that marker, and subsequently performing analysis, such as fluorescence measurements, of such a contacted cell to determine whether the antibody is bound the cell. Similarly, a cell is considered "negative" for a cell-surface marker if it does not express the marker on its cell-surface in amounts sufficient to be detected using methods known to those of skill in the art, such as contacting a cell with an antibody that binds specifically to that marker. In some embodiments, where agents specific for cell-surface lineage markers are used, the agents can all comprise the same label, such as fluorescent label, and thus all cells positive for that label can be collected, excluded or removed.

For use with the systems and methods described herein, preferred agents specific for cell-surface markers are targeting moiety such as antibody agents that specifically bind the cell-surface markers, and can include polyclonal and monoclonal antibodies, and antigen-binding derivatives or fragments thereof. Well-known antigen binding fragments include, for example, single domain antibodies (dAbs; which consist essentially of single $V_L$ or $V_H$ antibody domains), Fv fragment, including single chain Fv fragment (scFv), Fab fragment, and F(ab')2 fragment. Methods for the construction of such antibody molecules are well known in the art. Antigen-binding fragments can be produced by recombinant DNA techniques or by enzymatic or chemical cleavage of intact antibodies.

In some embodiments, a targeting moiety specific for a cell-surface molecule, such as an antibody or antigen-binding fragment, is labeled to facilitate the selection or isolation of the hematopoietic cell populations. The terms "label" or "tag," as used herein, refer to a composition capable of producing a detectable signal indicative of the presence of a target, such as, the presence of a specific cell-surface marker in a biological sample. Suitable labels include particles and beads, such as magnetic beads or particles or nanoparticles, nucleotide chromophores, enzymes, substrates, chemiluminescent moieties, magnetic particles, bioluminescent moieties, fluorescent molecules, nanoparticles, quantum dots, and the like.

In one embodiment, a detector as described herein can detect fluorescence, e.g., from a labeled antibody or other targeting moiety bound to a fraction or population of cells, or from a fluorescently labeled reagent introduced to cells as a surrogate marker for cell populations. Fluorescent detection can be used, for example, to detect the amount of a marker present in or on a population of cells in a sample. In such embodiments, the detector can, for example, detect the amount of the label in or associated with a given population. For example, the detector can detect cell number or the number of CD3 cells or the CD4:CD8 ratio.

In some embodiments, the systems and methods described herein permit assessment and/or adjustment of the cells.

In another embodiment, assessment and adjustments can be performed in a sampling unit. The sampling unit can, in some embodiments, interface with a detector module.

Exemplary assessments performed in the sampling unit include taking one or more measurements of a composition or chamber containing the cells, such as assessing cells for proliferation rate, degree of survival, phenotype, e.g., expression of one or more surface or intracellular markers, such as proteins or polynucleotides, and/or assessing the composition or chamber containing the cells for temperature, media component(s), oxygen or carbon dioxide content, and/or presence or absence or amount or relative amount of one or more factors, agents, components, and/or cell types, including subtypes. In some embodiments, the assessment is performed in an automated fashion, for example, using a detector module as described herein, and/or is set ahead of time to be carried out at certain time-points during incubation of the target cell populations with one or more customization agents. In some embodiments, the outcome of the assessment in the sampling unit, such as a determined interim ratio of two types of cells, indicates that one or more adjustments should be made, such as addition or removal of one or more cell types, or addition of additional customization agents.

In some embodiments, the outcome of the assessment in the sampling unit indicates that the target cell population has been sufficiently customized and can reenter the continuous, flow-through of the system.

Adjustments that can be made based on assessments done in the sampling unit can include adjusting any cell culture factor or parameter, such as temperature, length (time) for which incubation or a step thereof will be carried out (duration of incubation), replenishment, addition and/or removal of one or more components in the composition being incubated, e.g., media or buffer or components thereof, agents, e.g., nutrients, amino acids, antibiotics, ions, and/or stimulatory factors, such as cytokines, chemokines, antigens, binding partners, fusion proteins, recombinant soluble receptors, or cells or cell types or populations of cells. In some embodiments, the removal or addition of various components or other adjustment is carried out in an automated fashion, for example, using a device or system as described herein. In some embodiments, the system is programmed such that an adjustment is automatically initiated based on a certain readout from an interim assessment. For example, in some cases, the system described herein is programmed to carry out one or more assessments at a particular time; the system or device in such cases can be further programmed such that a particular outcome of such an assessment, such as a particular ratio of one cell type to another, initiates a particular adjustment, such as addition of one or more of the cell types, and/or output.

Preferably, any adjustments made based on assessments carried out in the sampling unit do not disrupt the closed environment of the other components and modules of the systems described herein. Accordingly, the cell customization module can further comprise additional input and/or removal conduits/valves/tubing, designed to add or remove components while maintaining sterility.

The sampling unit can permit the introduction, for example, of a substrate or indicator reagent. The sampling unit can also permit, for example, the introduction of a lysis reagent or can comprise, for example, a sonication probe that lyses cells, e.g., when a customizing enzyme is expressed intracellularly.

The patient-connected, closed-loop bedside systems described herein further comprise one or more detectors/detector modules that interface with the various modules or connections therebetween and/or with the patient/subject. Such detector modules monitor and detect various parameters to evaluate, control and/or regulate the flow of fluid and cells through the system and monitor the inputs and outputs of the various modules. Such detector modules can comprise sensors such as optical sensors, chemical sensors, temperature sensors, magnetic sensors, acoustic sensors, liquid sensors, bubble detectors (ultrasonic detector), pressure sensors, and the like.

The closed-loop system of the present disclosure includes the connection of multiple unit operations in sequence. The fluid, particulate, cells and/or combinations thereof generally exit a module in a changed state, i.e., a state that is different from the state the respective fluid, particulate, cells and/or combinations thereof was/were in when it entered the module. The nature of this changed state is often a matter of interest of the operators of the system. Efficient operation of the system and achievement of the objectives of the module are essential aspects. There are various reasons for this, including that the sample in its processed form is contained within the closed-loop patient connected system throughout the system's various processes and modules up until it introduced to the patient or subject. Detectors and detector modules are essential, therefore, to ensure that the processed sample and/or target cells is/are have met certain predetermined standards prior to certain junctures in the system. A juncture may be a decision point about whether the sample or a target cell (including collections of target cells) are approved to pass from one module (e.g., the purification module) to another module or to the patient in a condition appropriate, or more specifically target cells within the sample, to be placed in a condition for reintroduction to the patient or subject. Predetermined standards in this regard could be any condition discussed herein as an important or essential component of the functioning of the system or characteristics of the sample or cells within or between modules. Temperature, pH, cell count, target cell population purity, viscosity, cell size, viability, separation from particles, beads or bubbles, and/or sample impurity determinations, including combinations and sub-combinations thereof, among other aspects are included in the predetermined standards evaluated by the detectors of the present systems. Detectors may also be employed to ensure proper operation of the modules and the connections therebetween. For example, the systems may include detectors to ensure that all necessary tubing is connected, proper power levels are being received by the system, seals are in functional order, proper grounding is provided for the systems and the individual modules, sample-specific detectors are functional and have proper access to the sample, conduits are free of obstructions, reagents are properly placed and/or of sufficient volume and within lot expiration date periods, among a variety of other safety measures. Detectors are often provided intra-module as well, for example, as provided in detail herein, when performing cell purification using any of the number of procedures and reagents contemplated herein intermediate objectives are a consequence of the purification process. Such intermediate objectives ensure the purification within the module operates in a manner with predefined reagents types and concentrations, under the predefined conditions within the sample medium, and/or within predefined time periods. Detectors to monitor the status of the purification procedure with regard to these intermediate objectives, among others, are provided that create various decision points that are resolved automatically by the system and/or manual input from an operator of the system. It is contemplated that one or more various intermediate conditions are automatically resolved by the system to direct the system to further process the sample or pass the processed sample or target cells purified therefrom to another module or location in the system. One or more processors operably linked with a tangible storage medium and employing specialized software or firmware adapted for the detection and condition resolution processes are generally employed for module and system operations, including all such monitoring and resolution of conditions or intermediate conditions.

Such detectors are useful to determine, for example, if a sample exists the sample purification module and contains an unacceptable level of particles or beads used in the purification procedures. In this case such unacceptable level may often be zero, or a range of very low concentrations. If such a state is detected, a decision point is provided that may be automatically resolved or resolved through manual input. For example, the system may detect this state and then pass the sample to the same module or another module to reduce the sample to the acceptable levels of particles or beads.

As noted herein, sampling ports in the system are also optionally provided. Such ports are often sterile sampling ports and provide the opportunity for a user of the system to obtain a portion of the sample within the system for analysis outside of the system. Such ports may be provided before the sample purification module, within the sample purification module and/or in-line after the sample purification module. In operating such sampling ports, a portion of the sample is obtained and the portion is evaluated outside of the system for one or more pre-defined attributes that are deemed important to the operation of the system or its various processes and/or the status of the sample or its state of processing within the system.

For example, a camera, either focused on a macroscopic window of a cell separation module or focused, e.g., through a microscope objective onto a portion of a sample, can be used as a component of a detector module described herein to detect a sample that is being separated into at least two components during centrifugation. The camera as part of a detector module can be used to detect different layers formed by the separated sample in the cell separation module. In another embodiment, the detection system can determine turbidity or light transmissiveness as a surrogate for presence of cells. This detector can be used to determine cell concentration or when a unit operation and flow can be redirected or stopped. In a further embodiment, sensors to detect air bubbles can be included particularly as a safety element ensuring air is not returned to the patient. In another embodiment, sensors to detect the cell clumps or the presence of purification element (beads, particles, etc.) may be determined.

In some embodiments, a detector comprises a fluorescence detector, which comprises an incident light source of a given wavelength or wavelengths, and a detector that collects and quantifies fluorescent light emitted when incident light excites fluorescence at another wavelength. A fluorescence detector can be designed or arranged to detect fluorescence from any of a number of common fluorescent proteins or fluorescent labels, as the case may be. A luminescence detector may also be employed to identify predetermined or preselected luminescence reports.

In some embodiments of the detector modules described herein, a detector module is configured to detect hemoglobin in the plasma components of the blood. Detected hemoglobin signifies the presence of red blood cells in the plasma components of the blood. As the red blood cells are typically separated from the cellular components of the blood prior to cell customization, the presence of hemoglobin can be used to identify any issues with the cell purification module and/or modify output parameters from the cell purification module. Upon detection of hemoglobin, the circuitry can issue a warning, prevent return of fluids to the patient, and/or cease operation at least one module of the systems described herein.

Flow cell optical detection, or flow cytometric, components can also be used in some embodiments of the systems and methods described herein. How cell optical detection typically comprises a light (optical) source for providing light of one or more wavelengths to a fluid sample in a fluid cell and an optical detection system for detecting any interaction between the light and the sample. Light scattering is a phenomenon that occurs when there is a particle, such as a cell, that changes the traveling direction of light when the light hits it. Information about the size and material of the particle can be obtained by detecting the scattered light. Particularly, information about the size of the particle (cell) can be obtained from forward scattered light. Meanwhile, information about the inside of the particle, namely granularity of the cell, can be obtained from side scattered light. When a laser beam is applied to the cell, side scattered light intensity depends on the complexity (e.g., shape, size, and density of a nucleus, and an amount of granules) in the cell. For example, a device for performing flow cytometry, which refers to a technique for counting and examining microscopic particles, such as cells and chromosomes, by suspending them in a stream of fluid and passing them through an electronic detection apparatus, can optionally be used in the systems and methods described herein. Moreover, labeled reagents targeting a characteristic of the cells, such as an expressed receptor or protein, are also useful in flow cytometric analysis. When such reagents bind a target on the cell, they can be identified when irradiated by proper excitation wavelength light source. Multiple such targets can be identified on a single cell using different fluorescent labels and/or excitation wavelength light sources.

Detection systems useful with the systems and methods described herein include microfluidic-photonic integrated circuit optical interrogation devices, such as those described in U.S. Pat. No. 8,270,781, the contents of which are herein incorporated by reference. Such devices can include a photonic circuit integrated monolithically with microfluidic channels, such that the optical interrogation zones are in the proximity of and well aligned to the optical waveguides that collect fluorescence and/or scattering light signals. In some embodiments, multiple waveguides are employed to form an array waveguide structure so that, along the direction of flow, a particle (e.g., a cell) will pass a series of waveguide-defined optical interrogation zones, each producing a signal that is correlated in time and space to the others.

According to the presently contemplated bedside systems, a variety of kits are contemplated.

The presently contemplated kits include conduits for fluid flow between devices and/or modules of the system. Such kits also often include one or more fluid sampling port relative to the system noted elsewhere herein. The kits also often include reagents necessary for the cell purification such that additional reagents are not required to be added after connecting the kit with the system. The kits also include connectors to connect the kits in operable connection with the system to permit blood flow from the patient to the cell purification system, and passage of the blood, cells and/or blood components back to the patent in a patient-connected, closed-loop continuous-flow manner. Such kits also often include one or more areas for detector access to the kit or system while in use such that the cells or fluid flowing or resident in the system can be examined by the detector. The locations for such detector access and adaptations necessary to permit the desired type of detection (e.g., luminescence, fluorescence, light scatter, etc.) are in accordance with the locations described elsewhere herein.

It is understood that the systems described herein include circuitry and elements necessary to regulate and control the activities carried out in the various modules, the totality of which is termed herein the "processor module." The circuitry can include one or more of a microprocessor, or any other such component capable of controlling the activities carried out in the various modules, and a storage device or device capable of storing the data and/or transmitting data to a remote storage location. The remote location can be a local or remote server or databank, or a cloud-based storage system. In some embodiments, the circuitry can be operatively coupled to one or more input and output devices, for example an actuator, a motor-controlled valve, a motor, an accelerometer, a load sensor, a light source, or a light detector. In frequently contemplated embodiments, the systems contemplated herein include a graphical user interface (GUI) as one of a plurality of user-based input devices. The GUI may be imparted with a variety of functionalities, including actuation/control of the system, a module within the system, or a device within the system. As such, the GUI is placed in operable and/or data accessibility connection with the processor module. The systems also may be employed with accessibility from a remote location to control, monitor, and/or troubleshoot one or more components, modules, or devices in the system. The circuitry can comprise one or more microcontrollers. In some embodiments, the circuitry is configured to receive input from at least one module. Circuitry can be configured, for example, to cause a motor to adjust one or more valves controlling flow-through between the various modules, such that a fluid path is opened between the modules. In some embodiments, the circuitry causes the flow-through between two different modules to open and close after a pre-determined interval. In some embodiments, the total amount of time where flow-through is permitted between two given modules is tracked and/or stored by the circuitry. The processor module enables monitoring and process control of key activities including but not limited to in-line testing for quality, safety and other clinical purposes conducted, product dosing and cellular product quality conducted while patient-connected to cell separator (e.g. apheresis device) throughout process.

Some embodiments of the processor module include monitoring and/or recording and/or analyzing electronic signals. It is to be understood that such devices can include analog and/or digital signals. Thus, while a given module or component thereof sensor may be monitored and/or connected to circuitry, the circuitry can, in some embodiments, only intermittently sample, record, and or process such data. In some embodiments, continuous monitoring can include intermittent monitoring at set intervals.

In frequent embodiments the processor module is placed in operable connection with the cell purification module to control and/or monitor the status, operation and/or function of cell purification. Information obtained from a sampling unit may also be input to the processor module to record or adjust an aspect or function of device within the cell purification module. Often this is performed prior to a cell exiting the cell purification module.

Local and remote operation and/or monitoring of the system or a module or device located on the system are included in the presently contemplated embodiments. In this regard, aspects of the device including fluid flow positions, directions and rates, valve actuation, pump operation, conduit connectivity, consumable or kit connectivity or status, detector operation, cell resident times, incubation operation, time and status, purification operation, time and status, cell washing operation, incubator or temperature control mechanism operation, cell separation operation, cell enriching operation, processor and storage operation, may be local or remotely (via a wired or wireless control and data connection with the system) operated and/or monitored. Technicians, physicians, regulatory personnel, patients, and other medical care personnel may conduct such local or remote operation. While the system is bedside with the patient, one or more systems may be operated and/or monitored from a location remote from the patient, for example, at a health care staff monitoring/services station or within the local health care facility or remotely from a different location. In another example, a system technician or database accessible to such a technician, is provided with diagnostic or operation information from the system for maintenance or repair of the herein described systems through the processor.

Naturally given the contemplated fluid samples, in embodiments of the present disclosure, the system also often comprises a one or more pumps and valves responsible for moving sample fluid, samples containing purified target cells, and/or reagents through the system. While other types of pumps can be used, a peristaltic pump provides fluid transfer without undue shear forces introduced by some pumping mechanisms and is well suited for the transport of cells in and through the systems described herein. Other reagents can be transferred into and out of the various chambers, units and modules via peristaltic pump or via a mechanical pump, e.g., with an impeller.

It is to be understood that all embodiments contemplated herein are adapted for patient connected, closed sample loop, bedside use. These systems may be stand-alone systems or more frequently connected in a closed-loop with cellular therapy and/or cell modification systems as a specific cell purification module or modules within the cellular therapy and/or cell modification systems. PCT Publication No. WO2019217964, published Nov. 11, 2019, describes such exemplary cellular therapy and/or cell modification systems and is encompassed herein by reference.

According to a first embodiment, a patient-connected, closed-loop system for the purification of a target cell from a patient sample is provided, the system comprising: a) an inlet conduit adapted for parenteral communication with the patient and adapted for receiving blood from the patient; b) an apheresis or leukopheresis module in fluid connection with the inlet conduit; c) a targeting reagent comprising a substrate bound to a targeting moiety, wherein the targeting moiety is adapted to specifically bind or associate with the target cell; d) a cell purification module in fluid communication with the apheresis or leukopheresis module, the cell separation module comprising i.a mixing chamber configured to include at least one mixing chamber inlet fluidly coupled with the mixing chamber, wherein the at least one mixing chamber inlet is configured to store, guide or transport a liquid sample, the targeting reagent, or a combination of the liquid sample and the targeting reagent, to the mixing chamber; the mixing chamber further configured to include at least one mixing chamber outlet; ii. a mixing mechanism coupled with the mixing chamber and adapted to mix a content of the mixing chamber; iii. a collection chamber fluidly coupled with the at least one mixing chamber outlet, the collection chamber configured to include a collection chamber outlet, wherein the collection chamber is adapted to hold or transport a solution containing the target cell; iv. a detector configured to conduct an evaluation comprising a detection operation of a solution that has passed through the at least one mixing chamber outlet or the collection chamber outlet; v. at least one cell purification module outlet adapted to direct a solution from the at least one mixing chamber outlet or from the collection chamber outlet to the patient for parenteral administration of the solution or to a transfection module for modification of the target cell; e) a system outlet conduit in parenteral communication with the patient; and f) a processor configured to control an operation of the inlet conduit and/or the cell purification module; wherein the inlet conduit, each aspect of the cell purification module, the cell customization module, and the system outlet conduit are connected in a fluid-sealed closed-loop adapted for parenteral connection with the patient at both ends of the fluid sealed closed-loop, and the system is configured to permit obtaining the sample, cell purification to produce purified cells, and delivery of the purified cells to the patient within the fluid-sealed closed-loop.

According to a second embodiment, a patient-connected, closed-loop system for the purification of a target cell from a patient sample is provided, the system comprising: a) an inlet conduit adapted for parenteral communication with the patient and adapted for receiving blood from the patient; b) an apheresis or leukopheresis module in fluid connection with the inlet conduit; c) a targeting reagent comprising a substrate bound to a targeting moiety, wherein the targeting moiety is adapted to specifically bind or associate with the target cell; d) a cell purification module in fluid communication with the apheresis or leukopheresis module, the cell separation module comprising i. a separation chamber configured to include at least one separation chamber inlet fluidly coupled with the separation chamber, wherein the at least one separation chamber inlet is configured to store, guide or transport a liquid sample, the targeting reagent, or a combination of the liquid sample and the targeting reagent, to the separation chamber; the separation chamber further configured to include at least one separation chamber outlet; ii. a detector configured to conduct an evaluation comprising a detection operation of a solution that has passed through the separation chamber outlet; iii. at least one cell purification module outlet adapted to direct a solution from the at least one separation chamber outlet to the patient for parenteral administration of the solution or to a transfection module for modification of the target cell; e) a system outlet conduit in parenteral communication with the patient; and f) a processor configured to control an operation of the inlet conduit and/or the cell purification module; wherein the inlet conduit, each aspect of the cell purification module, the cell customization module, and the system outlet conduit are connected in a fluid-sealed closed-loop adapted for parenteral connection with the patient at both ends of the fluid sealed closed-loop, and the system is configured to permit obtaining the sample, cell purification to produce purified cells, and delivery of the purified cells to the patient within the fluid-sealed closed-loop.

According to a third embodiment, the system of embodiments 1-2 further comprises an electromagnetic element positioned adjacent to the separation chamber and adapted to apply a magnetic field to a content of the separation chamber.

According to a fourth embodiment, the system of any embodiments 1-3, and further comprising a pump in operable communication with the at least one mixing chamber outlet or the at least one separation chamber outlet.

According to a fifth embodiment, the system of any embodiments 1-4 is present, wherein the at least one mixing chamber outlet comprises a first and a second mixing chamber outlet, wherein the first mixing chamber outlet is fluidly coupled with the collection chamber, and the second mixing chamber outlet is fluidly coupled directly with the system outlet or the at least one mixing chamber inlet.

According to a sixth embodiment, the system of any embodiments 1-5 is present, wherein the targeting moiety is an antibody having a specificity for a cell surface marker.

According to a seventh embodiment, the system of any embodiments 1-6 is present, wherein the detector comprises an opacity sensor.

According to an eighth embodiment, the system of any embodiments 1-7 is present and further comprises the cell customization module.

According to a ninth embodiment, the system of any embodiments 1-8 is present, wherein the substrate comprises a microbubble, a bead, or a nanoparticle.

According to a tenth embodiment, the system of any embodiments 1-9 is present and further comprises an apheresis module or a leukopheresis module positioned in-line between the inlet conduit and the cell purification module and in fluid communication with the inlet conduit and the cell purification module.

According to an eleventh embodiment, the system of any embodiments 1-10 is present, wherein the evaluation comprises detecting a concentration or number of target cells, evaluating the sample for the presence or absence of the substrate, evaluating the sample for the percentage or amount of enrichment of the target cell in the sample.

According to a twelfth embodiment, the system of any embodiments 1-11 is present, wherein the substrate is a microparticle or microbubble.

According to a thirteenth embodiment, a method for purifying a target cell from a patient blood sample in a closed-loop system is provided, comprising; connecting a parenteral inlet adapted to parenterally receive blood from the patient; permitting the blood to pass through the parenteral inlet to an apheresis or leukopheresis module to provide a sample containing a target cell; permitting the sample containing the target cell to pass through the parenteral inlet to a cell purification module; introducing a targeting reagent comprising a substrate bound to a targeting moiety to the blood from the patient, or fraction thereof, before or after the blood from the patient enters the cell purification module; permitting the targeting reagent to bind the target cell in the blood from the patient, or fraction thereof, to create a target cell/reagent complex in the cell purification module; separating the target cell/reagent complex from the blood from the patient, or fraction thereof; optionally separating the target cell from the targeting reagent to create a separated target cell; and returning the separated target cell to the patient via a parenteral outlet adapted to parenterally administer the separated target cell to the patient, wherein each of the steps occurs in the closed-loop system devoid manual intervention such that each step occurs without removing the blood from the patient or any component of the blood from the patient from the closed-loop system.

According to a fourteenth embodiment, the method of embodiment 13 is provided and further includes a transfection or transformation of the target cell occurs before returning the separated target cell to the patient via a parenteral outlet.

According to a fifteenth embodiment, the method of embodiments 13-14 is provided, wherein the separated target cell comprises a plurality of separated target cells in a solution, and wherein the plurality of separated target cells are present in the solution at a concentration that is enriched for the target cell at least at or about 50% more than the target cell was present in the blood from the patient.

According to a sixteenth embodiment, the method of embodiments 13-15 is provided, wherein the plurality of separated target cells are present in the solution at a concentration that is enriched for the target cell between about 50% to about 90% more than the target cell was present in the blood from the patient.

According to a seventeenth embodiment, the method of embodiments 13-16 is provided, wherein the targeting reagent is incubated with the blood from the patient, or fraction thereof, for between at or about 5 minutes to at or about 15 minutes.

According to an eighteenth embodiment, the method of embodiments 13-17 is provided and further comprises permitting the blood from the patient to pass from the parenteral inlet to an apheresis module or a leukopheresis module to remove non-nucleated cells and create the fraction thereof of the blood prior, and permitting the fraction thereof to pass to the cell purification module.

According to a nineteenth embodiment, the method of embodiments 13-18 is provided and further comprises permitting the separated target cell or the target cell/reagent complex to pass to a transfection module for cell modification to produce a modified cell prior to returning the modified cell to the patient via a parenteral outlet.

According to a twentieth embodiment, the method of embodiments 13-19 is provided, wherein the target cell/reagent complex is separated from the blood from the patient, or fraction thereof, using buoyancy, magnetic force, acoustic force, or electrophoretic force.

According to a twenty first embodiment, the method of embodiments 13-20 is provided, wherein each step of the recited steps occurs in a predefined time period.

According to a twenty second embodiment, the method of embodiments 13-21 is provided, wherein the predefined time period is selected from the group consisting of: between at or about 5 minutes to at or about 30 minutes, between at or about 10 minutes to at or about 60 minutes, between at or about 15 minutes to at or about 90 minutes, between at or about 5 minutes to at or about 15 minutes, between at or about 10 minutes to at or about 45 minutes, between at or about 15 minutes to at or about 30 minutes, between at or about 20 minutes to at or about 45 minutes, and between at or about 5 minutes to at or about 90 minutes.

According to a twenty third embodiment, the method of embodiments 13-22 is provided, wherein each of the recited steps occurs in a total predefined time period.

According to a twenty fourth embodiment, the method of embodiments 13-23 is provided, wherein the total predefined time period is selected from the group consisting of: between at or about 2 hours to at or about 6 hours, between at or about 2 hours to at or about 4 hours, between at or about 2 hours to at or about 3 hours, between at or about 3 hours to at or about 4 hours, between at or about 4 hours to at or about 5 hours, between at or about 5 hours to at or about 6 hours, and less than 2 hours.

According to a twenty fifth embodiment, the method of embodiments 13-24 is provided and further comprises monitoring the closed-loop system or the sample in or between each recited step and determining if the closed-loop system is functioning properly and/or if the sample or the target cell meets a predetermined intermediate objective.

According to a twenty sixth embodiment, the method of embodiments 13-25 is provided, wherein in the condition where the sample is determined not to meet the predetermined intermediate objective, the sample is directed to undergo an additional processing until it meets the predetermined intermediate objective.

According to a twenty seventh embodiment, the method of embodiments 13-26 is provided, wherein the directing of the sample to undergo an additional processing is provided automatically and without human intervention.

According to a twenty eighth embodiment, the method of embodiments 13-27 is provided, wherein the introducing, permitting and separating steps comprise a two-step purification process, wherein non-target cells are separated from the target cell, and the target cell comprises a plurality of separated target cells in a solution, and wherein the plurality of separated target cells are present in the solution at a concentration that is enriched for the target cell at least at or about 50% more than the target cell was present in the blood from the patient.

According to a twenty ninth embodiment, the method of embodiments 13-28 is provided, wherein the targeting reagent is a microbubble, and the microbubble is separated from the target cell to create the separated target cell.

According to a thirtieth embodiment, the method of embodiments 13-29 is provided, wherein the targeting reagent is a microbead or microparticle, and the microbead or microparticle is separated from the target cell using a filtration system or a particle separation system to create the separated target cell.

According to a thirty first embodiment, the method of embodiments 13-30 is provided, wherein the particle separation system comprises a magnetic particle separation system and the targeting reagent comprises a nanomagnetic particle.

According to a thirty third embodiment, the method of embodiments 13-31 is provided, wherein the magnetic particle separation system comprises an electromagnetic chip adapted to include one or more individually addressable electromagnetic units.

According to a thirty fourth embodiment, the method of embodiments 13-33 is provided, wherein the microbubble is separated from the target cell using one or more of applying overpressure, creating underpressure, ultrasonication, contact with a detergent, contact with a surfactant, through a pH change.

According to a thirty fifth embodiment, the method of embodiments 13-34 is provided, wherein the target cell/reagent complex is separated from the blood or a processed component thereof in a solution by decantation, transfer from one syringe to another, skimming cell/reagent complexes from a layer of the solution, or introduction of the target cell/reagent complex to a two phase system comprised of immiscible low density fluid into which the microbubble/target component complexes will float.

According to a thirty sixth embodiment, the method of embodiments 13-35 is provided, wherein the microbubble is a functionalized microbubble comprising one or more reactive groups, linkers, ligands, or targeting moieties adapted for specific binding to a target cell.

According to a thirty seventh embodiment, the method of embodiments 13-36 is provided, wherein the functionalized microbubble comprises a ligand present on the microbubble surface on the order of 100,000 ligands or more per microbubble.

According to a thirty eighth embodiment, the method of embodiments 13-37 is provided, wherein the functionalized microbubble has a diameter of between 50 nm to 100 μm.

According to a thirty ninth embodiment, the method of embodiments 13-38 is provided, wherein the functionalized microbubble comprises a coalescence-resistant surface membrane (e.g., gelatin), a filmogenic protein (e.g., albumin, gamma globulin, apotransferrin, hemoglobin, collagen, urease, human serum albumin, etc.), a filmogenic protein mixed with a polymer (e.g., albumin/dextran), a polymer material (natural or synthetic or modified), an elastic interfacial synthetic polymer membrane, a microparticulate biodegradable polyaldehyde, a microparticulate N-dicarboxylic acid derivative of a polyamino acid-polycyclic imide, a lipid, a protein, a surfactant, a phospholipid, a lipopeptide, a phosphatidylcholine, a stearic acid, a palmitic acid, a PEGylated ceramide, a PEGylated fatty acid, or a combination of two or more of the foregoing.

According to a fortieth embodiment, the method of embodiments 13-39 is provided, wherein the cell modification comprises cell modification using zinc finger nucleases (ZFN), transcription activator-like effector nucleases (TALEN), Clustered Regularly Interspaced Short Palindromic Repeats (CRISPR), CRISPR-associated (Cas) systems, lipid nanoparticles comprising mRNA, modified mRNAs (mmRNAs), small interfering RNA (siRNA), micro RNA (miRNA), antisense oligonucleotides, ribozymes, plasmids, immune-stimulating nucleic acids, antisense RNAs, antagomir, antimir, microRNA mimic, supermir, U1 adaptors, and/or aptamers.

According to a forty first embodiment, the method of embodiments 13-40 is provided, wherein the targeting reagent is a microbubble, and the microbubble is separated from the target cell to create the separated target cell.

According to a forty second embodiment, the method of embodiments 13-41 is provided, wherein the microbubble is a functionalized microbubble comprising one or more reactive groups, linkers, ligands, or targeting moieties adapted for specific binding to a target cell.

According to a forty third embodiment, the method of embodiments 13-42 is provided, wherein the functionalized microbubble comprises a coalescence-resistant surface membrane (e.g., gelatin), a filmogenic protein (e.g., albumin, gamma globulin, apotransferrin, hemoglobin, collagen, urease, human serum albumin, etc.), a filmogenic protein mixed with a polymer (e.g., albumin/dextran), a polymer material (natural or synthetic or modified), an elastic interfacial synthetic polymer membrane, a microparticulate biodegradable polyaldehyde, a microparticulate N-dicarboxylic acid derivative of a polyamino acid-polycyclic imide, a lipid, a protein, a surfactant, a phospholipid, a lipopeptide, a phosphatidylcholine, a stearic acid, a palmitic acid, a PEGylated ceramide, a PEGylated fatty acid, or a combination of two or more of the foregoing.

According to a forty fifth embodiment, the method of embodiments 1-12 is provided, wherein the bead is not a DYNAL bead.

According to a forty sixth embodiment, the method of embodiments 1-12 or 45 is provided, wherein the substrate is a functionalized microbubble comprising one or more reactive groups, linkers, ligands, or targeting moieties adapted for specific binding to a target cell.

According to a forty seventh embodiment, the method of embodiments 1-12 or 45-46 is provided, wherein the functionalized microbubble comprises a ligand present on the microbubble surface on the order of 100,000 ligands or more per microbubble.

According to a forty eighth embodiment, the method of embodiments 1-12 or 45-47 is provided, wherein the functionalized microbubble has a diameter of between 50 nm to 100 μm.

According to a forty ninth embodiment, the method of embodiments 1-12 or 45-48 is provided, wherein the functionalized microbubble comprises a coalescence-resistant surface membrane (e.g., gelatin), a filmogenic protein (e.g., albumin, gamma globulin, apotransferrin, hemoglobin, collagen, urease, human serum albumin, etc.), a filmogenic protein mixed with a polymer (e.g., albumin/dextran), a polymer material (natural or synthetic or modified), an elastic interfacial synthetic polymer membrane, a microparticulate biodegradable polyaldehyde, a microparticulate N-dicarboxylic acid derivative of a polyamino acid-polycyclic imide, a lipid, a protein, a surfactant, a phospholipid, a lipopeptide, a phosphatidylcholine, a stearic acid, a palmitic acid, a PEGylated ceramide, a PEGylated fatty acid, or a combination of two or more of the foregoing.

According to a fiftieth embodiment, the method of embodiments 1-12 or 45-49 is provided, wherein the cell customization module is adapted to conduct cell modification using zinc finger nucleases (ZFN), transcription activator-like effector nucleases (TALEN), Clustered Regularly Interspaced Short Palindromic Repeats (CRISPR), CRISPR-associated (Cas) systems, lipid nanoparticles comprising mRNA, modified mRNAs (mmRNAs), small interfering RNA (siRNA), micro RNA (miRNA), antisense oligonucleotides, ribozymes, plasmids, immune-stimulating nucleic acids, antisense RNAs, antagomir, antimir, microRNA mimic, supermir, U1 adaptors, and/or aptamers.

The above examples and embodiments are included for illustrative purposes only and are not intended to limit the scope of the disclosure. Many variations to those methods, systems, kits, and devices described above are possible. Since modifications and variations to the examples described above will be apparent to those of skill in this art, it is intended that this invention be limited only by the scope of the appended claims. All publications and references cited herein are expressly incorporated herein by reference in their entirety and/or for the specific reason for which they are cited herein.

The invention claimed is:

1. A method for purifying a target cell from a patient blood sample in a closed-loop system, comprising;
   connecting a parenteral inlet adapted to parenterally receive blood from the patient;
   permitting the blood to pass through the parenteral inlet to an apheresis or leukopheresis module to provide a sample containing a target cell;
   permitting the sample containing the target cell to pass through the parenteral inlet to a cell purification module;
   introducing a targeting reagent comprising a substrate bound to a targeting moiety to the blood from the patient, or a fraction thereof, before or after the blood from the patient enters the cell purification module;
   permitting the targeting reagent to bind the target cell in the blood of the patient, or fraction thereof, to create a target cell/reagent complex in the cell purification module;
   separating the target cell/reagent complex from the blood from the patient, or fraction thereof;
   separating the target cell from the targeting reagent to create a separated target cell; and
   returning the separated target cell to the patient via a parenteral outlet adapted to parenterally administer the separated target cell to the patient,
   wherein each of the steps occur in the closed-loop system devoid of manual interventions such that each step occurs without removing the blood from the patient or any component of the blood from the patient from the close-loop system.

2. The method of claim 1, wherein the separated target cell comprises a plurality of separated target cells in a solution, and wherein the plurality of separated target cells are present in the solution at a concentration that is enriched for the target cell at least at or about 50% more than the target cell was present in the blood from the patient.

3. The method of claim 1, wherein the separated target cell comprises a plurality of separated target cells in a solution, and wherein the plurality of separated target cells are present in the solution at a concentration that is enriched for the target cell at least at 50% more than the target so is present in the blood from the patient;

wherein the targeting reagent is incubated with the blood from the patient, or fraction thereof, for between at or about five minutes to at or about 15 minutes;

wherein the method further comprises permitting the blood from the patient to pass from the parenteral inlet to an apheresis module or a leukopheresis module to remove non-nucleated cells and create the fraction thereof of the blood prior, and permitting the fraction thereof to pass to the cell purification module; and permitting the separated target cell or target cell/reagent complex to pass to a transfection module for cell modification to produce a modified cell prior to returning them modified cell to the patient via a parenteral outlet.

4. The method of claim 3, wherein the target cell/reagent complex is separated from the blood from the patient, or fraction thereof, using buoyancy, magnetic force, acoustic force, or electrophoretic force.

5. The method of claim 4, wherein each of the recited steps occurs in a total predefined time period.

6. The method of claim 4, further comprising monitoring the closed-loop system or the sample in or between each recited step and determining if the closed-loop system is functioning properly and/or if the sample or the target cell meets a predetermined intermediate objective, wherein in the condition where the sample is determined not to meet the predetermined intermediate objective, the sample is directed to undergo an additional processing until it meets the predetermined intermediate objective.

7. The method of claim 6, wherein the directing of the sample to undergo an additional processing is provided automatically and without human intervention.

8. The method of claim 1, wherein the introducing, permitting and separating steps comprise a two-step purification process, wherein non-target cells are separated from the target cell, and the target cell comprises a plurality of separated target cells in a solution, and wherein the plurality of separated target cells are present in the solution at a concentration that is enriched for the target cell at least at or about 50% more than the target cell was present in the blood from the patient.

9. The method of claim 1, wherein (a) the targeting reagent is a microbubble, and the microbubble is separated from the target cell to create the separated target cell, and/or (b) the targeting reagent is a microbead or microparticle, and the microbead or microparticle is separated from the target cell using a filtration system or a particle separation system to create the separated target cell.

10. The method of claim 9, wherein the microbubble is separated from the target cell using one or more of applying overpressure, creating underpressure, ultrasonication, contact with a detergent, contact with a surfactant, through a pH change.

11. The method of claim 10, wherein the target cell/reagent complex is separated from the blood or a processed component thereof in a solution by decantation, transfer from one syringe to another, skimming cell/reagent complexes from a layer of the solution, or introduction of the target cell/reagent complex to a two phase system comprised of immiscible low density fluid into which the microbubble/target component complexes will float.

* * * * *